US008658780B2

(12) United States Patent
Pierce et al.

(10) Patent No.: US 8,658,780 B2
(45) Date of Patent: *Feb. 25, 2014

(54) TRIGGERED COVALENT PROBES FOR IMAGING AND SILENCING GENETIC EXPRESSION

(75) Inventors: Niles A. Pierce, Pasadena, CA (US); Jeffrey Robert Vieregg, Studio City, CA (US)

(73) Assignee: California Institute of Technology, Pasadena, CA (US)

( * ) Notice: Subject to any disclaimer, the term of this patent is extended or adjusted under 35 U.S.C. 154(b) by 32 days.

This patent is subject to a terminal disclaimer.

(21) Appl. No.: 13/016,811

(22) Filed: Jan. 28, 2011

(65) Prior Publication Data

US 2011/0288148 A1 Nov. 24, 2011

Related U.S. Application Data

(60) Provisional application No. 61/345,939, filed on May 18, 2010.

(51) Int. Cl.
*C07H 21/04* (2006.01)
*C12Q 1/68* (2006.01)

(52) U.S. Cl.
USPC ........................ 536/24.3; 435/6.12

(58) Field of Classification Search
None
See application file for complete search history.

(56) References Cited

U.S. PATENT DOCUMENTS

| | | | |
|---|---|---|---|
| 4,714,680 A | 12/1987 | Civin | |
| 4,897,355 A | 1/1990 | Eppstein et al. | |
| 4,965,204 A | 10/1990 | Civin | |
| 5,057,410 A | 10/1991 | Kawasaki et al. | |
| 5,061,620 A | 10/1991 | Tsukamoto et al. | |
| 5,118,801 A | 6/1992 | Lizardi et al. | |
| 5,270,163 A | 12/1993 | Gold et al. | |
| 5,312,728 A | 5/1994 | Lizardi et al. | |
| 5,424,413 A | 6/1995 | Hogan et al. | |
| 5,459,127 A | 10/1995 | Felgner et al. | |
| 5,563,256 A | 10/1996 | Chakraborty et al. | |
| 5,579,793 A | 12/1996 | Gajewski et al. | |
| 5,643,741 A | 7/1997 | Tsukamoto et al. | |
| 5,677,136 A | 10/1997 | Simmons et al. | |
| 5,691,145 A | 11/1997 | Pitner et al. | |
| 5,716,827 A | 2/1998 | Tsukamoto et al. | |
| 5,750,397 A | 5/1998 | Tsukamoto et al. | |
| 5,928,913 A | 7/1999 | Efstathiou et al. | |
| 5,989,823 A | 11/1999 | Jayasena et al. | |
| 6,242,246 B1 | 6/2001 | Gold et al. | |
| 6,261,783 B1 | 7/2001 | Jayasena et al. | |
| 6,361,944 B1 | 3/2002 | Mirkin et al. | |
| 6,361,945 B1 | 3/2002 | Becker et al. | |
| 6,485,965 B1 | 11/2002 | Klatzmann et al. | |
| 6,506,559 B1 | 1/2003 | Fire et al. | |
| 6,555,367 B1 | 4/2003 | Spence et al. | |
| 6,899,871 B2 | 5/2005 | Kasahara et al. | |
| 7,033,834 B2 | 4/2006 | Valerio et al. | |
| 7,632,641 B2 | 12/2009 | Dirks et al. | |
| 7,727,721 B2 | 6/2010 | Pierce et al. | |
| 7,960,357 B2 | 6/2011 | Dirks et al. | |
| 8,105,778 B2 | 1/2012 | Dirks et al. | |
| 8,124,751 B2 * | 2/2012 | Pierce et al. | 536/24.3 |
| 8,241,854 B2 | 8/2012 | Yin et al. | |
| 8,318,921 B2 | 11/2012 | Pierce et al. | |
| 2002/0051769 A1 | 5/2002 | Zhang | |
| 2002/0172950 A1 | 11/2002 | Kenny et al. | |
| 2003/0092162 A1 | 5/2003 | Shankara et al. | |
| 2003/0129611 A1 | 7/2003 | Bao et al. | |
| 2004/0009510 A1 | 1/2004 | Seiwert et al. | |
| 2004/0043386 A1 | 3/2004 | Pray et al. | |
| 2004/0126773 A1 | 7/2004 | Beske et al. | |
| 2004/0223953 A1 | 11/2004 | Kung et al. | |
| 2005/0089864 A1 | 4/2005 | Li et al. | |
| 2005/0112614 A1 | 5/2005 | Cook | |
| 2005/0239061 A1 | 10/2005 | Marshall et al. | |
| 2005/0260635 A1 | 11/2005 | Dirks et al. | |
| 2006/0035375 A1 | 2/2006 | Head et al. | |
| 2006/0088864 A1 | 4/2006 | Smolke et al. | |
| 2006/0228733 A1 * | 10/2006 | Pierce et al. | 435/6 |
| 2006/0234261 A1 | 10/2006 | Pierce et al. | |
| 2007/0087334 A1 | 4/2007 | Dirks et al. | |

(Continued)

FOREIGN PATENT DOCUMENTS

EP 0 273 085 7/1988
EP 1 479 766 11/2004

(Continued)

OTHER PUBLICATIONS

Pieles, U. et al. Psoralen covalently linked oligodeoxyribonucleotides: synthesis, sequence specific recognition of DNA and photo-cross-linking pyrimidine residues of DNA. Nucleic Acids Research, vol. 17, p. 285-299, 1989.*
Aagaard et al., "RNAi Therapeutics: Principles, Prospects and Challenges." *Advanced Drug Delivery Reviews* 59 (2007): 75-86.
Allan et al., "A Concise Total Synthesis of (-)-Quinocarcin via Aryne Annulation." *Journal of American Chemical Society* 130 (2008) 17270-17271.
Amarzguioui et al., "Rational design and in vitro and in vitro delivery of Dicer substrate siRNA,", Nature Protocols, vol. 1, No. 2, pp. 508-517, 2006.
Behenna et al., "The Enantioselective Tsuji Allylation." *Journal of American Chemical Society* 126.46 (2004): 15044-15045.

(Continued)

*Primary Examiner* — Prabha Chunduru
(74) *Attorney, Agent, or Firm* — Knobbe, Martens, Olson & Bear, LLP

(57) ABSTRACT

The present invention relates to the use of cross-linking probes to covalently bind probes to nucleic acid targets. In some embodiments, the probe comprises an initiator region that is able to bind to a first portion of a target nucleic acid, a probe region linked too the initiator region that is able to bind to a second region of the target nucleic acid and that comprises one or more cross-linkers, and a blocking region hybridized to the probe region.

12 Claims, 11 Drawing Sheets

(56) References Cited

U.S. PATENT DOCUMENTS

| | | | |
|---|---|---|---|
| 2007/0117109 | A1 | 5/2007 | Rothemund |
| 2008/0214488 | A1 | 9/2008 | Pierce et al. |
| 2009/0011956 | A1 | 1/2009 | Yin et al. |
| 2009/0123914 | A1 | 5/2009 | Erikson et al. |
| 2009/0197271 | A1 | 8/2009 | Kotlikoff et al. |
| 2009/0247615 | A1 | 10/2009 | Pierce et al. |
| 2009/0311799 | A1 | 12/2009 | Sotzing et al. |
| 2010/0021901 | A1* | 1/2010 | Yin et al. ............ 435/6 |
| 2010/0021904 | A1 | 1/2010 | Pierce et al. |
| 2010/0035233 | A1 | 2/2010 | Yin et al. |
| 2010/0047926 | A1 | 2/2010 | Dirks et al. |
| 2011/0104676 | A1 | 5/2011 | Pierce et al. |
| 2011/0287557 | A1 | 11/2011 | Zhang et al. |
| 2011/0288148 | A1 | 11/2011 | Pierce et al. |
| 2011/0288832 | A1 | 11/2011 | Pierce et al. |
| 2011/0313030 | A1 | 12/2011 | Dirks et al. |
| 2012/0021410 | A1 | 1/2012 | Yin et al. |
| 2012/0022243 | A1 | 1/2012 | Yin et al. |
| 2012/0022244 | A1 | 1/2012 | Yin |
| 2012/0190835 | A1 | 7/2012 | Pierce et al. |
| 2012/0251583 | A1 | 10/2012 | Rothemund |

FOREIGN PATENT DOCUMENTS

| | | |
|---|---|---|
| EP | 1 634 890 | 3/2006 |
| EP | 2 055 781 | 5/2009 |
| EP | 1 730 161 | 9/2010 |
| EP | 1 931 806 | 10/2011 |
| WO | WO 92/03464 | 3/1992 |
| WO | WO 94/01550 | 1/1994 |
| WO | WO 99/31276 | 6/1999 |
| WO | WO 01/40516 | 6/2001 |
| WO | WO 2005/098049 | 10/2005 |
| WO | WO 2006/048025 | 5/2006 |
| WO | WO 2007/008276 | 1/2007 |
| WO | WO 2007/044727 | 4/2007 |
| WO | WO 2007044727 A2 * | 4/2007 |
| WO | WO 2008/106658 | 2/2008 |
| WO | WO 2008/144562 | 5/2008 |
| WO | WO 2011/126996 | 4/2011 |

OTHER PUBLICATIONS

Bloomfield et al., "Nucleic Acids: Structures, Properties, and Functions." *University Science Books* (2000).

Bois et al., "Topological constraints in nucleic acid hybridization kinetics", Nucleic Acids Research, vol. 33, No. 13, pp. 4090-4095, 2005.

Bolt et al., Differential Reactivities of the mono- and di-epoxide of 1,3-butadiene. *Toxicology* 113 (1996): 294-296.

Bumcrot et al., "RNAi Therapeutics: A Potential New Class of Pharmaceutical Chemical Biology Drugs." *Nature Chemical Biology* 2.12 (Dec. 2006): 711-719.

Bushnell et al., "ProbeDesigner: for the design of probesets for branched DNA (bDNA) signal amplification assays," Bioinformatics, 15(5), pp. 348-355, 1999.

Caltech News Release, "Caltech Scientists Create New Process to Program", Sep. 6, 2010.

Caplen, "RNAi as a gene therapy approach", Expert Opin. Biol. Ther., vol. 3, No. 4, pp. 575-586, 2003.

Castanotto et al., "The Promises and Pitfalls of RNA-Interface-Based Therapeutics." *Nature* 457 (Jan. 22, 2009):426-433.

Cerutti et al., "On the Origin and Functions of RNA-Mediated Silencing: From Protists to Man." *Current Genetics* 50 (2006) 81-99.

Check, "RNA to the rescue?", Nature, vol. 425, pp. 10-12, Sep. 4, 2003.

Coburn et al., "siRNAs: a new wave of RNA-based therapeutics", Journal of Antimicrobial Chemotherapy, vol. 51, pp. 753-756, 2003.

Coleman, R.S. and Pires, R.M. Covalent cross-linking of duplex DNA using 4-thio-2'-deoxyuridine as a readily modifiable platform for introduction of reactive functionality into oligonucleotides. Nucleic Acids Research, 1997. 25: p. 4771-4777.

Coleman et al., "Template-Directed Corss-Linking of Oligonucleotides: Site-Specific Covalent Modification of dG-N7 Within Duplex DNA." J. Org. Chem. 60 (1995): 6252-6253.

Collins et al., "A branched DNA signal amplification assay for quantification of nucleic acid targets below 100 molecules/ml," Nucleic Acids Res, 25(15), pp. 2979-2984, 1997.

Coppelli et al., "Oligonucleotides as Anticancer Agents: From the Benchside to the Clinic and Beyond", Current Pharmaceutical Design, vol. 11, pp. 2825-2840, 2005.

Cullen et al., "Genome-wide Screening for Gene Function Using RNAi in Mammalian Cells." *Immunology and Cell Biology* 83 (2005) 217-223.

Czauderna et al., "Structural Variations and Stabilising Modifications of Synthetic siRNAs in Mammalian Cells." *Nucleic Acids Research* 31.11 (2003): 2705-2716.

Definition for "substantial" from Merriam-Webster Online Dictionary. Downloaded from merriam-webster.com; downloaded on Mar. 5, 2008.

Dias et al., "Antisense Oligonucleotides: Basic Concepts and Mechanisms." *Molecular Cancer Therapeutics* 1 (Mar. 2002) 347-355.

Dirks et al., "An Algorithm for Computing Nucleic Acid Base-Pairing Probabilities Including Pseudoknots." *Journal of Computational Chemistry* 25.10 (2004): 1295-1304.

Dirks et al., "A Partition Function Algorithm for Nucleic Acid Secondary Structure Including Pseudoknots." *Journal of Computational Chemistry* 24.13 (2003) 1664-1677.

Dirks et al., "Paradigms for computational nucleic acid design," Nucleic Acids Research, vol. 32, No. 4, pp. 1392-1403, Oxford University Press, 2004.

Dirks et al., "Thermodynamic Analysis of Interacting Nucleic Acid Strands." *SIAM Review* 49.1 (2007): 65-88.

Dirks et al., "Triggered amplification by hybridization chain reaction," PNAS, vol. 101, No. 43, pp. 15275-15278, Oct. 26, 2004.

Dohjima, T. et al., "Small Interfering RNAs Expressed from a Pol III Promoter Suppress the EWS/Fli-1 Transcript in an Ewing Sarcoma Cell Line", Molecular Therapy, vol. 7, No. 6, pp. 811-816, Jun. 2003.

Elbashir et al., "Functional anatomy of siRNAs for mediating efficient RNAi in *Drosophila melanogaster* embryo lysate", The EMBO Journal, vol. 20, No. 23, pp. 6877-6888, 2001.

Elghanian et al.,"Selective colorimetric detection of polynucleotides based on the distance-dependent optical properties of gold nanoparticles," Science, 277 (5329), pp. 1078-1081, 1997.

Ellington et al., "In vitro selection of RNA molecules that bind specific ligands," Nature 346, pp. 818-822, 1990.

Elmén et al., "Locked Nucleic Acid (LNA) Mediated Improvements in siRNA Stability and Functionality." *Nucleic Acids Research* 33.1 (2005): 439-447.

Enquist et al.., "The Total Synthesis of ( - )- Cyanthiwigin F by Means of Double Catalytic Enantioselective Alkylation." *Nature* 453.7199 (Jun. 26, 2008) 1228-1231.

Extended European Search Report from Application No. 08755764. 1, dated Nov. 7, 2011.

Felgner, et al., "Nomenclature for Synthetic Gene Delivery Systems", Human Gene Therapy, vol. 8, pp. 511-512, Mar. 20, 1997.

Femino et al., "Visualization of Single Molecules of mRNA in Situ." *Methods of Enzymology* 361 (2003): 245-304.

Ferkol et al., "Gene Transfer into the Airway Epithelium of Animals by Targeting the Polymeric Immunoglobulin Receptor", J. Clin. Invest., vol. 95, pp. 493-502, Feb. 1995.

Ferkol et al., "Regulation of the phosphoenolpyruvate carboxykinase/human factor IX gene introduced into the lives of adult rats by receptor-mediated gene transfer", The FASEB Journal, vol. 7, pp. 1081-1091, Aug. 1993.

Ferreira et al., "The Palladium-Catalyzed Oxidative Kinetic Resolution of Secondary Alcohols with Molecular Oxygen." *Journal of American Chemical Society* 123.31 (2001): 7725-7726.

Final Office Action dated Sep. 20, 2010 for U.S. Appl. No. 12/454,799.

Final Office Action dated Sep. 17, 2010 for U.S. Appl. No. 12/467,755.

Final Office Action dated Oct. 15, 2010 for U.S. Appl. No. 12/152,893.

(56) References Cited

OTHER PUBLICATIONS

Final Office Action dated Jul. 15, 2011 for U.S. Appl. No. 12/040,735.
Final Office Action dated Jul. 25, 2011 for U.S. Appl. No. 12/395,489.
Fire et al., "Potent and specific genetic interference by double-stranded RNA in *Caenorhabditis elegans*", Nature, vol. 391, pp. 806-811, Feb. 19, 1998.
Flamm et al., "RNA folding at elementary step resolution," RNA, vol. 6, pp. 325-338, 2000.
Friedrich et al., A Cellular Screening Assay to Test the Ability of PKR to Induce Cell Death in Mammalian Cells, Molecular Therapy, vol. 12, No. 5, pp. 969-975, Nov. 2005.
Friedrich et al., "RNA molecules as anti-cancer agents", Seminars in Cancer Biology, vol. 14, pp. 223-230, 2004.
Garcia et al., "Impact of Protein Kinase PKR in Cell Biology: from Antiviral to Antiproliferative Action." Microbiology and Molecular Biology Reviews vol. 70, No. 4 (Dec. 2006): pp. 1032-1060.
Garg et al., "Development of an Enantiodivergent Strategy for the Total Synthesis of (+)- and (−)-Dragmacidin F from a Single Enantiomer of Quinic Acid." *Journal of American Chemical Society* 127 (2005) 5970-5978.
Garg et al., "A Ligand-free Solid-supported System for Sonogashira Couplings: Applications in Nucleoside Chemistry." *Chem. Commun.* (2005) 4551-4553.
Gilman et al., "The Biological Actions and Therapeutic Applications of the B-Chloroethyl Amines and Sulfides." *Science* 103.2675 (Apr. 5, 1946): 409-415.
Hashimoto et al., "Recent Progress in Diazirine-Based Photoaffinity Labeling." *Eur. J. Org. Chem.* (2008): 2513-2523.
Haugland RP. The Handbook: A Guide to Fluorescent Probes and Labeling Technologies. 10th Ed. Molecular Probes/Invitrogen; 2005.
Hearst et al., "Psoralen Photochemistry." *Ann.Rev. Biophys.Bioeng.* 10 (1981): 69-86.
Heidel, J.D., "Targeted, systematic non-viral delivery of small interfering RNA in vivo", Doctoral thesis, California Institute of Technology, pp. 1-128, 2005.
Herath et al., "Synthesis of Acrimarins from 1,3,5-Trioxygenated-9-acridone Derivatives." *Journal of Heterocyclic Chem.* 41 (2004): 23-28.
Higuchi et al. Selective regulation of mutant K-ras mRNA expression by photo-cross-linking antisense oligonucleotide. Nucleic Acids Symposium Series (2007) vol. 51 (1) pp. 443-444.
Hofacker et al., "Fast folding and comparison of RNA secondary structures," Monatshefte für Chemie, vol. 125, pp. 167-188, 1994.
Hokaiwado et al., "RNAi-based drug discovery and its application to therapeutics", IDrugs, vol. 11, No. 4, pp. 274-278, 2008.
Hu-Lieskovan et al., "Sequence-Specific Knockdown of EWS-FLI1 by Targeted, Nonviral Delivery of Small Interfering RNA Inhibits Tumor Growth in a Murine Model of Metastatic Ewing's Sarcoma." *Cancer Research* 65.19 (Oct. 1, 2005): 8984-8992.
Hughes et al., "Double Labeling wit Fluorescence in Situ Hybridization in *Drosophila* Whole-Mount Embryos," BioTechniques, 24(4), pp. 530-532, 1998.
Huizenga et al., "A DNA Aptamer That Binds Adenosine and ATP." Biochemistry 34, pp. 656-665, 1995.
International Search Report and Written Opinion from PCT/US2005/009471, dated Mar. 8, 2006.
International Search Report and Written Opinion from PCT/US2008/055559, dated Sep. 3, 2008.
Iqbal et al., "A review of molecular recognition technologies for detection of biological threat agents", Biosensors & Bioelectronics, vol. 15, pp. 549-578, 2000.
Jagus et al., "PKR, apoptosis and cancer", The International Journal of Biochemistry & Cell Biology, vol. 31, pp. 123-138, 1999.
Jhaveri et al., "In vitro selection of signaling aptamers", Nature Biotechnology, vol. 18, pp. 1293-1297, Dec. 2000.
Judge et al., "Design of Noninflammatory Synthetic siRNA Mediating Potent Gene Silencing in Vivo." *Molecular Therapy* 13.3 (Mar. 2006): 494-505.
Judge et al., "Overcoming the Innate Immune Response to Small Interfering RNA", Human Gene Therapy, vol. 19, pp. 111-124, Feb. 2008.
Julian et al., "Biomimetic Approaches to Gas Phase Peptide Chemistry: Combining Selective Binding Motifs with Reactive Carbene Precursors to Form Molecular Mousetraps." *International Journal of Mass Spectrometry* 228 (2003): 851-864.
Julian et al., "Molecular Mousetraps: Gas-Phase Studies of the Covalent Coupling of Noncovalent Complexes Initiated by Reactive Carbenes Formed by Controlled Activation of Diazo Precursors." *Agnew. Chem. Int. Ed.* 42.9 (2003) 1012-1015.
Kadnikov et al., "Synthesis of Coumarins via Palladium—Catalyzed Carbonylative Annulation of Internal Alkynes by o-Iodophenols." *Organic Letters* 2.23 (2000): 3643-3646.
Killops, K.L., Campos, L.M., Hawker, C.J. Robust, Efficient, and Orthogonal Synthesis of Dendrimers via Thiol-ene "Click" Chemistry. Journal of the American Chemical Society, 2008. 130: p. 5062-5064.
Kim et al., "Synthetic dsRNA Dicer substrates enhance RNAi potency and efficacy", Nature Biotechnology, vol. 23, No. 2, pp. 222-226, Feb. 2005.
Kim et al., "Strategies for Silencing Human Disease Using RNA Interference." *Nature Review Genetics* 8 (Mar. 2007) 173-184.
Kislauskis et al. "Isoform-specific 3'-untranslated Sequences Sort ά-cardiac and β-cytoplasmic Actin Mesenger RNAs to Different ytoplasmic Compartments," The Journal of Cell Biology, 123(1), pp. 165-172, 1993.
Knorre et al., "Photoaffinity Labeling as an Approach to Study Supramolecular Nucleoprotein Complexes." *FEBS Letters* 433 (1998): 9-14.
Kobertz et al., "An Efficient Synthesis of a Furan-Side Furocoumarin Thymidine Monoadduct." *J. Org. Chem.* 62.8 (1997) 2630-2632.
Kobertz et al., "Solid-Phase Synthesis of Oligonucleotides Containing a Site-Specific Psoralen Derivative." *Journal of American Chemical Society* 119 (1997): 5960-5961.
Kobertz et al., "Total Synthesis of a Cis-Syn 2-Carbomethoxypsoralen Furan-Side Thymidine Monoadduct." *Journal of American Chemical Society* 118 (1996): 7101-7107.
Kosman, et al., "Multiplex Detection of RNA Expression in *Drosophila* Embryos," Science, 305, p. 846, 2004.
Lacenere et al., "Effects of a Modified Dye-Labeled Nucleotide Spacer Arm on Incorporation by Thermophilic DNA Polymerases." *Nucleosides, Nucleotides, and Nucleic Acids* 25 (2006) 9-15.
Ladiges, et al., "Tissue specific expression of PKR protein kinase in aging B6D2F1 mice," Mechanisms of Ageing and Development, vol. 114, pp. 123-132, (2000).
Lawley et al., "DNA Adducts from Chemotherapeutic Agents." *Mutation Research—Fundamental and Molecular mechanisms of Mutagenesis* 355 (1996): 13-40.
Lawrence et al., "Highly Localized Tracks of Specific Transcripts within Interphase Nuclei Visualized by in Situ Hybridization," Cell, 57, pp. 493-502, 1989.
Layzer et al., "In Vivo Activity of Nuclease-Resistant siRNAs." *RNA* 10 (2004): 766-771.
Levsky et al., "Single-Cell Gene Expression Profiling," Science 297, pp. 836-840, 2002.
Liu et al., "A colorimetric lead biosensor using DNAzyme-directed assembly of gold nanoparticles," J. Am. Chem. Soc., 125(22), pp. 6642-6643, 2003.
Macechko et al., "Comparison of Immunologic Amplification vs Enzymatic Deposition of Fluorochrome-conjugated Tyramide as Detection Systems for FISH," J Histochem Cytochem, 45(3), pp. 359-363, 1997.
Mahato et al., "Modulation of gene expression by antisense and antigene oligodeoxynucleotides and small interfering RNA", Expert Opin. Drug Deliv., vol. 2, No. 1, pp. 3-28. 2005.
Manche et al., "Interactions between Double-Stranded RNA Regulators and the Protein Kinase DAI", Molecular and Cellular Biology, vol. 12, No. 11, pp. 5238-5248, Nov. 1992.
Manoharan et al., "RNA Interference and Chemically Modified Small Interfering RNAs." *Current Opinion in Chemical Biology* 8 (2004): 570-579.

(56) References Cited

OTHER PUBLICATIONS

Matsui, T. et al., "Expression of Unphosphorylated Form of Human Double-Stranded RNA-Activated Protein Kinase in *Escherichia coli*", Biochemical and Biophysical Research Communications, vol. 284, No. 3, pp. 798-807, 2001.

Meinhardt et al., "Wavelength-dependent Penetration Depths of Ultraviolet Radiation in Human Skin." Journal of Biomedical Optics 13.4 (Jul./Aug. 2008) 044030-1-044030-5.

Mittelstadt, et al., "Interaction of human tRNA-dihydrouridine synthase-2 with interferon-induced protein kinase PKR," Nucleic Acids Research, vol. 36, No. 3, pp. 998-1008, (2008).

Mohr et al., "Catalytic Enantioselective Decarboxylative Protonation." *Journal of American Chemical Society* 128.35 (2006): 11348-11349.

Mohr et al., "Natural Products as Inspiration for the Development of Asymmetric Catalysis." *Nature* 455 (Sep. 18, 2008) 323-332.

Nakano et al., "Selection for thermodynamically stable DNA tetraloops using temperature gradient gel electrophoresis reveals four motifs: d(cGNNAg), d(cGNABg), d(cCNNGg), and d(gCNNGc)," Biochemistry, vol. 41, pp. 14281-14292, American Chemical Society, 2002.

Naked Scientists (The): Science Radio & Science Podcasts, "RNA-away cancer cells", Sep. 12, 2010, http://www.thenakedscientists.com/HTML/content/news/news/2051/.

National Science Foundation, "These Cells Will Self-Destruct in Five . . . Four . . . ", Press Release 10-160, p. 1-3.

Noll et al., "Formation and Repair of Interstrand Cross-Links in DNA." *Chemical Reviews* 106.2 (2006) 277-301.

Noll et al., "Preparation of Interstrand Cross-Linked DNA Oligonucleotide Duplexes." *Frontiers in Bioscience* 9 (Jan. 1, 2004): 421-437.

Nutiu et al., "Structure-switching signaling aptamers," J. Am. Chem. Soc., vol. 125, pp. 4771-4778, American Chemical Society, 2003.

Office Action dated Feb. 4, 2010 in U.S. Appl. No. 12/152,893.

Office Action dated Apr. 1, 2010 in U.S. Appl. No. 12/467,755.

Office Action dated Nov. 9, 2010 for U.S. Appl. No. 12/040,735.

Office Action dated Dec. 16, 2010 for U.S. Appl. No. 12/395,489.

Office Action dated Mar. 10, 2011 in U.S. Appl. No. 12/454,743, filed May 22, 2009.

Office Action dated Mar. 17, 2011 for U.S. Appl. No. 12/611,875.

Opalinska et al., "Nucleic-Acid Therapeutics: Basic Principles and Recent Applications", Nature Reviews Drug Discovery, vol. 1, pp. 503-514, 2002.

Perales et al., "Gene Transfer in vivo: Sustained Expression and Regulation of Genes Introduced into the Liver by Receptor-Targeted Uptake", Proceedings of the National Academy of Sciences of the United States of America, vol. 91, pp. 4086-4090, Apr. 1994.

Pieles, U. and Englisch, U. Psoralen covalently linked to oligodeoxyribonucleotides: synthesis, sequence specific recognition of DNA and photo-cross-linking to purimidine residues of DNA. Nucleic Acids Research, 1989. 17: p. 285-299.

Player et al., "Single-copy Gene Detection Using Branched DNA (bDNA)) in Situ Hybridization," J. Histochem & Cytochem, 49(5), pp. 603-611, 2001.

Pouton et al., "Key issues in non-viral gene delivery", Advanced Drug Delivery Reviews, vol. 46, pp. 187-203, 2001.

Qian et al., "Recent Developments in Signal Amplification Methods for in Situ Hybridization," Diagnostic Molecular Pathology, 12(1), pp. 1-13, 2003.

Qian, X., L. Jin, and R.V. Lloyd, in situ hybridization: basic approaches and recent development. The Journal of Histotechnology, 2004. 27(1): p. 53-67.

Rachofsky et al., "Probing structure and dynamics of DNA with 2-aminopurine: Effects of local environment on fluorescence," Biochemistry, vol. 40, pp. 946-956, 2001.

Raj et al., "Imaging Individual mRNA Molecules Using Multiple Singly Labeled Probes." *Nature Methods* 5.10 (Oct. 2008): 877-879.

Read et al., "Barriers to Gene Delivery Using Synthetic Vectors", Advances in Genetics, vol. 53, pp. 19-46, 2005.

Reynolds et al., "Rational siRNA Design for RNA Interference." *Nature Biotechnology* 22.3 (Mar. 2004) 326-330.

Saunders et al., "Introduction of DNA into Bacteria." *Methods in Microbiology* 29 (1999): 3-49.

Schärer et al., "DNA Interstrand Crosslinks: Natural and Drug-Induced DNA Adducts that Induce Unique Cellular Responses." *ChemBioChem* 6 (2005): 27-32.

Scherer et al., "Approaches for the sequence-specific knockdown of mRNA", Nature Biotechnology, vol. 21, No. 12, pp. 1457-1465, 2003.

Schipani, Vanessa, "A targeted cancer therapy?" The Scientist, Sep. 7, 2010 blog post, http://www.the-scientist.com/blog/display/57674/.

Schulte-Merker et al., "no tail (ntl) is the zebrafish homologue of the mouse T (Brachyury) gene." Development 120 (1994): 1009-1015.

Schwartz et al., "Cloning and Functional Analysis of Multiply Spliced mRNA Species of Human Immunodeficiency Virus Type 1", Journal of Virology, vol. 64, No. 6, pp. 2519-2529, Jun. 1990.

Schweitzer et al., "Combining nucleic acid amplification and detection," Curr Opin Biotechnol, 12, pp. 21-27, 2001.

Seelig et al., "Catalyzed Relaxation of a Metastable DNA Fuel", Journal American Chemical Society, vol. 128, No. 37, pp. 12211-12220, 2006.

Seeman, "DNA in a material world", Department of Chemistry, New York University, Nature, vol. 421, pp. 427-431 (Jan. 23, 2003).

Seeman, "Nucleic acid junctions and lattices," J. Theor. Biol., vol. 99, pp. 237-247, Academic Press Inc. (London) Ltd., 1982.

Seeman, "Nucleic acid nanstructures and topology", Angew. Chem. Int. Ed. vol. 37, pp. 3220-3238 (1998).

Shah et al., "The Fries Isomerization of Acetyl and Benzoyl Esters of Umbelliferones." *J. Org. Chem.* 19 (1954): 1681-1685.

Shir et al., "Inhibition of glioma growth by tumor-specific activation of double-stranded RNA-dependent protein kinase PKR", Nature Biotechnology, vol. 20, pp. 895-900, Sep. 2002.

Silverman et al., "Oligonucleotide Probes for RNA-Targeted Fluorescence in Situ Hybridization." *Advances in Clinical Chemistry* 43 (2007): 79-115.

Silverman et al., "Quenched Autoligation Probes Allow Discrimination of Live Bacterial Species by Single Nucleotide Differences in rRNA." *Nucleic Acids Research* 33.15 (2005): 4978-4986.

Siolas et al., "Synthetic shRNAs as Potent RNAi Triggers." *Nature Biotechnology* 23.2 (Feb. 2005): 227-231.

Sokol et al., "Real time detection of DNA•RNA hybridization in living cells", Proc. Natl. Acad. Sci. USA, vol. 95, pp. 11538-11543, Sep. 1998.

Storhoff et al., "One-pot colorimetric differentiation of polynucleotides with single base imperfections using gold nanoparticles," J. Am. Chem. Soc., 120, pp. 1959-1964, 1998.

Sun et al., "Side Chain Chemistry Mediates Backbone Fragmentation in Hydrogen Deficient Peptide Radicals." *Journal of Proteome Research* 8 (2009) 958-966.

Supplementary European Search Report from PCT/US2005/009471, dated May 6, 2008.

Takei et al., "A Small Interfering RNA Targeting Vascular Endothelial Growth Factor as Cancer Therapeutics." *Cancer Research* 64. (May 15, 2004): 3365-3370.

Tani et al., "Synthesis and Structural Analysis of 2-Quinuclidonium Tetrafluoroborate." *Nature* 441 (Jun. 8, 2006) 731-734.

Thomas et al., "Photoaffinity Cross-Linking and RNA Structure Analysis." *Methods in Enzymology* 318 (2000) 136-147.

Tijsterman et al., "Dicers at RISC: The Mechanism of RNAi", Cell, vol. 117, pp. 1-3, 2004.

Tuerk et al., "Systematic Evolution of Ligands by Exponential Enrichment: RNA Ligands to Bacteriophage T4 DNA Polymerase," Science 249, pp. 505-510, 1990.

U.S. File History for U.S. Appl. No. 12/790,379.

Vermeulen et al., "The contributions of dsRNA structure to Dicer specificity and efficiency", RNA, vol. 11, pp. 674-682, 2005.

Vodovozova et al., "Photoaffinity Labeling and Its Application in Structural Biology." *Biochemistry* (Moscow) 72.1 (2007): 1-20.

(56) References Cited

OTHER PUBLICATIONS

Volker, et al., "Conformational energetics of stable and metastable states formed by DNA triple repeat oligonucleotides: implications for triplet expansion diseases," PNAS, vol. 99, No. 23, pp. 14700-14705, Nov. 12, 2002.
Voorhoeve et al., "Knockdown Stands Up.:" *Trends in Biotechnology* 21.1 (Jan. 2003) 2-4.
Wagner et al., "Transferrin-Polycation Conjugates as Carriers for DNA Uptake into Cells", Proceedings of the National Academy of Sciences of the United States of America, vol. 87, pp. 3410-3414, May 1990.
Wassarman et al., "Psoralen Crosslinking of Small RNAs in vitro." *Molecular Biology Reports* 17 (1993): 143-151.
White et al., "The Catalytic Asymmetric Total Synthesis of Elatol" *Journal of American Chemical Society* 130.3 (2008): 810-811.
Wijen et al., "The in vivo Genetic Activity Profile of the Monofunctional Nitrogen Mustard 2-Chloroethylamine Differs Drastically from its Bifunctional Counterpart Mechlorethamine." *Carcinogenesis* 21.10 (2000) 1859-1867.
Wilkie et al., "Transcribed genes are localized according to chromosomal position within polarized *Drosophila* embryonic nuclei," Current Biology, 9, pp. 1263-1266, 1999.
Williams, B.R.G., "PKR; a sentinel kinase for cellular stress", Oncogene, vol. 18, pp. 6112-6120, 1999.
Willis, M.C., et al. Photocross-linking of 5-lodouracil-Substituted RNA and DNA to Proteins. Science, 1993. 262: p. 1255-1257.
Wu et al., "A Model for the Double-stranded RNA (dsRNA)-dependent Dimerization and Activation of the dsRNA-activated Protein Kinase PKR", The Journal of Biological Chemistry, vol. 272, No. 2, pp. 1291-1296, 1997.
Wu et al., "Receptor-mediated in Vitro Gene Transformation by a Soluble DNA Carrier System", The Journal of Biological Chemistry, vol. 262, No. 10, pp. 4429-4432, 1987.
Yin et al., "Programming biomolecular self-assembly pathways", Nature, vol. 451, pp. 318-323, Jan. 17, 2008.
Yoshimura et al., "Interstrand Photocrosslinking of DNA via p-carbamoylvinyl Phenol Nucleoside." *Bioorganic & Medicinal Chemistry Letters* 15 (2005): 1299-1301.
Yurke et al., "A DNA-fuelled molecular machine made of DNA", Letters to Nature, vol. 406, pp. 605-608 (Aug. 10, 2000).
Zheng et al., "Activation of the protein kinase PKR by short double-stranded RNAs with single-stranded tails", RNA, vol. 10, pp. 1934-1945, 2004.
Zhou et al., "RNA Interference and Potential Applications", Current Topics in Medicinal Chemistry, vol. 6, pp. 901-911, 2006.
Zuker et al., "Optimal computer folding of large RNA sequence using thermodynamics and auxiliary information," Nucleic Acids Research, vol. 9, No. 1, pp. 133-147, 1981.
Turberfield, et al., DNA fuel for free-running nanomachines, Physical Review Letters, vol. 90, No. 11, pp. 118102-1-118102-4, Mar. 21, 2003.
Tyagi et al., "Molecular Beacons: Probes that Fluoresce upon Hybridization," Nature Biotechnology 14, pp. 303-308, 1996.
U.S. File History printed Jun. 16, 2009 for U.S. Appl. No. 11/087,937, filed Mar. 22, 2005, entitled "Hybridization Chain Reaction,".
U.S. File History printed Jun. 16, 2009 for U.S. Appl. No. 11/371,346, filed Mar. 7, 2006, entitled "Hybridization Chain Reaction Amplification for in Situ Imaging,".
U.S. File History printed Jun. 16, 2009 for U.S. Appl. No. 11/371,347, filed Mar. 7, 2006, entitled "Colorimetric Readout of Hybridization Chain Reaction,".
U.S. File History printed Jun. 16, 2009 for U.S. Appl. No. 11/544,306, filed Oct. 6, 2006, entitled "PKR Activation Via Hybridization Chain Reaction,".
U.S. File History printed Jun. 16, 2009 for U.S. Appl. No. 12/040,735, Feb. 29, 2008, entitled "Triggered RNAi,".
U.S. File History printed Jun. 16, 2009 for U.S. Appl. No. 12/152,893, filed May 16, 2008, entitled "A Versatile Nucleic Acid Hairpin Motif for Programming Biomolecular Self-Assembly Pathways,".
U.S. File History printed Jun. 4, 2010 for U.S. Appl. No. 12/611,875, filed Nov. 3, 2009, entitled "Hybridization Chain Reaction,".
U.S. File History printed Jun. 4, 2010 for U.S. Appl. No. 12/395,489, filed Feb. 27, 2009, entitled "Triggered RNAi,".
U.S. File History printed Jun. 4, 2010 for U.S. Appl. No. 12/454,799, filed May 22, 2009, entitled "Compositions and Methods for Detecting Analytes,".
U.S. File History printed Jun. 4, 2010 for U.S. Appl. No. 12/467,755, May 18, 2009, entitled "Shielded Cross-Linking Probes,".
U.S. File History printed Jun. 4, 2010 for U.S. Appl. No. 12/454,743, filed May 22, 2009, entitled "Triggered RNAi,".
U.S. File History for U.S. Appl. No. 12/790,379, Jan. 19, 2012.
Van De Corput et al., "Sensitive mRNA Detection by Fluorescence in Situ Hybridization Using Horseradish Peroxidase-labeled Oligodeoxynucleotides and Tyramide Signal Amplification," J. Histochem Cytochem, 46(11), pp. 1249-1259, 1998.
Venkataraman et al., "An Autonomous Polymerization Motor Powered by DNA Hybridization." *Nature Nanotechnology* 2 (Aug. 2007): 490-494.
Venkataraman et al. "Selective Cell Death Mediated by Small Conditional RNAs", Proc Natl Acad Sci USA, early edition, approved Jul. 21, 2010, p. 1-6.
Venkataraman et al. Abstract of "Selective Cell Death Mediated by Small Conditional RNAs", Proc Natl Acad Sci USA, early edition, http://www.pnas.org/content/early/2010/09/01/1006377107.abstract.
Andronescu et al., "A New Algorithm for RNA Secondary Structure Design", J. Mol. Biol., vol. 336, pp. 607-624, 2004.
Asbury, C.L., "Kinesin: world's tiniest biped, Current Opinion in Cell Biology", vol. 17, pp. 89-97, 2005.
Barish, R.D.; Schulman, R.; Rothemund, P.W.K.; Winfree, E., "An Information-Bearing seed for nucleating algorithmic self assembly." Proceedings of the National Academy of Sciences 2009, 106, 6054.
Bates, M.; Huang, B.; Dempsey, G.T.; and Zhuang, X. "Multicolor super-resolution imaging with photo-switchable fluorescent probes." Science, 317: 1749-1759, 2007.
Butterfoss et al., Computer-Based Design of Novel Protein Structures, Annu. Rev. Biophys. Biomol. Struct., vol. 35, pp. 49-65, 2006.
Chen Y.; Liu, H.P.; Ye, T.; Kim, J.; Mao, C.D. "DNA-Directed Assembly of Single—Wall Carbon Nanotubes." J.Am. Chem. Soc. 2007,129.
Dietz et al., "Folding DNA into Twisted and Curved Nanoscale Shapes." Science 2009, 325, 725-730.
Douglas et al., "DNA-nanotube-induced alignment of membrane proteins for NMR structure determination", PNAS, vol. 104, No. 16, pp. 6644-6648, Apr. 17, 2007.
Douglas et al., "Self-assembly of DNA into nanoscale three-dimensional shapes", Nature, vol. 459, pp. 414-418, May 21, 2009.
Eckstein, F. "Phosphrothioate oligodeoxynucleotides: what is their origin and what is unique about them?" Antisense Nucleic Acid Drug Dev., 10:117-121, 2000.
Eddy, S.R. "Non-coding RNA genes and the modern RNA world." Nature Reviews, 2: 919-929, 2001.
Communication Article 94(3) EPC from Application No. 08755764.1, dated Nov. 7, 2012.
Extended European Search Report dated Apr. 22, 2010 in European Patent Application No. 06836249.0.
Feldkamp et al., "Rational Design of DNA Nanoarchitectures", Angew. Chem. Int. Ed., vol. 45, pp. 1856-1876, 2006.
Fu et al., "DNA Double-Crossover Molecules", Biochemistry, vol. 32, pp. 3211-3220, 1993.
File History of U.S. Appl. No. 11/544,306, May 27, 2010.
File History for U.S. Appl. No. 13/186,228, Jan. 24, 2013.
File History of U.S. Appl. No. 13/186,331, Aug. 8, 2013.
File History of U.S. Appl. No. 13/186,315, Aug. 2, 2013.
Final Office Action dated May 27, 2010 for U.S. Appl. No. 11/544,306.
Green et al., "DNA Hairpins: Fuel for Autonomous DNA Devices", Biophysical Journal, vol. 91, pp. 2966-2975, Oct. 2006.

(56) References Cited

OTHER PUBLICATIONS

Hansma et al., "DNA Binding to Mica Correlates with Cationic Radius: Assay by Atomic Force Microscopy", Biophysical Journal, vol. 70, pp. 1933-1939, Apr. 1996.
Hell, S.W. "Far-field optical nanoscopy." Science, 316: 1153-1158, 2007.
Final Office Action dated Jun. 28, 2013 for U.S. Appl. No. 13/186,228.
Kuzuya et al., "Six-Helix and Eight-Helix DNA Nanotubes Assembled from Half-Tubes", Nano Lett., vol. 7, No. 6, pp. 1757-1763, 2007.
Le et al., "DNA-Templated Self-Assembly of Metallic Nanocomponent Arrays on a Surface", Nano Lett., vol. 4, No. 12, pp. 2343-2347, 2004.
Lee et al., "A self-replicating peptide", Nature, vol. 382, pp. 525-528, Aug. 8, 1996.
Levy et al., "Exponential growth by cross-catalytic cleavage of deoxyribozymogens", PNAS, vol. 100, No. 11, pp. 6416-6421, May 27, 2003.
Li, H.; LaBean, T.H.; Kenan, D.J. " Single-chain antibodies against Dna aptamers for use as adapter molecules on Dna tile arrays in nanoscale materials organization." Organic and Biomolecular Chemistry 2006, 3420-3426. 2006.
Li, Z, Trimble, M.J.; Brun, Y.V.; Jensen, G.J. "The structure of FtsZ filaments in vivo suggests a force-generating role in cell division." Embo J.,26, pp. 4694-4708. 2007.
Lin et al., "DNA Tile Based Self-Assembly: Building Complex Nanoarchitectures", ChemPhysChem, vol. 7, pp. 1641-1647, 2006.
Liu et al., "Approaching the Limit: Can One DNA Oligonucleotide Assemble into Large Nanostructures?", Angew. Chem. Int. Ed., vol. 45, pp. 1942-1945, 2006.
Liu et al., "DNA nanotubes self-assembled from triple-crossover tiles as templates for conductive nanowires", PNAS, vol. 101, No. 3, pp. 717-722, Jan. 20, 2004.
Mathieu et al., "Six-Helix Bundles Designed from DNA", Nano Lett., vol. 5, No. 4, pp. 661-665, 2005.
Mitchell et al., "Self-Assembly of Chiral DNA Nanotubes", J. Am. Chem. Soc., vol. 126, pp. 16342-16343, 2004.
Office Action dated Apr. 16, 2010 in U.S. Appl. No. 12/454,799.
Office Action dated Oct. 14, 2011 for U.S. Appl. No. 12/454,743.
Office Action dated Jan. 24, 2013 for U.S. Appl. No. 13/186,228.
Office Action dated Aug. 8, 2013 for U.S. Appl. No. 13/186,331.
Office Action dated Aug. 2, 2013 for U.S. Appl. No. 13/186,315.
Park et al., "Rapid Identification of Candida dubliniensis Using a Species-Specific Molecular Beacon", Journal of Clinical Microbiology, vol. 38, No. 8, pp. 2829-2836, 2000.
Paul et al., "A self-replicating ligase ribozyme", PNAS, vol. 99, No. 20, pp. 12733-12740, Oct. 1, 2002.
Piston, D.W., and Gremersa, G.J. "Fluorescent protein FRET: the good, the bad and the ugly." Trends in Biochemical Sciences, 32, 2007.
Qi et al., "Surface Transfer Doping of Diamond (100) by Tetrafluorotetracyanoquinodimethane", J. Am. Chem. Soc., vol. 129, pp. 8084-8085, 2007.
Reif J.H.; Sahu, S.; Yin, P. "Compact Error-Resilient Computational DNA tiling Assemblies." in Proc. $10^{th}$ International Meeting on DNA Computing; 2004.
Reif, J.H.; Sahu, S.; Yin, P. "Complexity of Graph Self-Assembly in Accretive Systems and Self-Destructible Systems." in Proc. $11^{th}$ International Meeting on DNA Computing; 2005.
Rothemund, P.; Papadakis, J.; Winfree, E. "Algorithmic Self-Assembly of DNA Sierpinski Triangles." PLoS Biology 2004, 2, 2041-2053.
Rothemund et al., "Design and Characterization of Programmable DNA Nanotubes", J. Am. Chem. Soc., vol. 126, pp. 16344-16352, 2004.
Rothemund, P.W.K.; Winfree, E. "The Program-size complexity of self-assembled squares (extended abstract)." In Proceedings of the thirty-second annual ACM symposium on Theory of computing; ACM Press: 2000.
Sahu et al., "A self-Assembly Model of Time-Dependent Glue Strength." In Proc. 11th International Meeting on DNA Computing; 2005.
Schulman et al., "Synthesis of crystals with a programmable kinetic barrier to nucleation", PNAS, vol. 104, No. 39, pp. 15236-15241, Sep. 25, 2007.
Seeman, "De Novo Design of Sequences for Nucleic Acid Structural Engineering", Journal of Biomolecular Structure & Dynamics, pp. 573-581, vol. 8, No. 3, 1990.
Sekulic, A.; Hudson, C.C; Homme, J.L.; Yin, P.; Otterness, D.M.; Karnitz, L.M.; Abraham, R.T. A Direct Linkage between the Phosphoinositide 3-Kinase-AKT Signaling Pathway and the Mammalian Target of Rapamycin in Mitogen-stimulated and Transformed Cells. Cancer Research 2000, 60, 3504-3513.
Sharma et al., "DNA-Tile-Directed Self-Assembly of Quantum Dots into Two-Dimensional Nanopatterns", Angew. Chem. Int. Ed., vol. 47, pp. 5157-5159, 2008.
Shih et al., "A 1.7-kilobase single-stranded DNA that folds into a nanoscale octahedron", Nature, vol. 427, pp. 618-621, Feb. 12, 2004.
Thompson, N.L.; Lieto, A.M., and Allen, N. W. "Recent advances in fluorescence correlation spectroscopy." Curr. Opin.Struct. Biol., 12, 2002.
Turk, Greg and Levoy, Marc. "Zippered polygon meshes from range images." in Siggraph, pp. 311-318, 1994.
Tyagi, et al., Multicolor Molecular Beacons for Allele Discrimination, Nature Biotechnology vol. 16, pp. 49-53, Jan. 1998.
Von Kiedrowski, "A Self-Replicating Hexadeoxynucleotide", Agnew. Chem. Int. Ed. Engl., vol. 25, No. 10, pp. 932-935, 1986.
Winfree et al., "Design and self-assembly of two-dimensional DNA crystals", Nature, vol. 394, pp. 539-544, Aug. 6, 1998.
Winfree, E. Algorithmic Self-Assembly of DNA, Ph.D. thesis. Thesis, California Institute of Technology, 1998.
Yan et al., "DNA-Templated Self-Assembly of Protein Arrays and Highly Conductive Nanowires", Science, vol. 301, pp. 1882-1884, Sep. 26, 2003.
Zhang, L., Zhou, W., Velculescu, V.E.; Kern, S.E., Hruban, R.H., Hamilton, S.R.; Vogelstein, B.; and Kinzler, K.W. "Gene expression profiles in normal and cancer cells." Science, 276:1268-1272, 1997.
Zhang et al., Targeted Gene Silencing by Small Interfering RNA-Based Knock-Down Technology, Current Pharmaceutical Biotechnology, vol. 5, pp. 1-7, 2004.
Notice of Allowance dated Feb. 20, 2013 for U.S. Appl. No. 12/395,489.
Notice of Allowance dated Apr. 4, 2013 for U.S. Appl. No. 13/363,022.

* cited by examiner

TRIGGERED COVALENT PROBES FOR IMAGING AND SILENCING GENETIC EXPRESSION

CROSS-REFERENCE TO RELATED APPLICATIONS

The present application claims priority to U.S. Provisional Application No. 61/345,939, filed May 18, 2010, which is hereby incorporated by reference in its entirety.

STATEMENT REGARDING FEDERALLY SPONSORED R&D

This invention was made with government support under grant nos. NIH 5R01EB006192-04 and NIH P50 HG004071 awarded by the National Institutes of Health. The government has certain rights in this invention.

SEQUENCE LISTING

The present application is being filed along with a Sequence Listing in electronic format. The Sequence Listing is provided as a file entitled Seqence_Listing-CALTE051A, created, Jan. 27, 2011, which is 1,661 bytes in size. The information in the electronic format of the Sequence Listing is incorporated herein by reference in its entirety.

BACKGROUND

1. Field

The present disclosure relates to the covalent cross-linking of nucleic acid probes to target nucleic acids.

2. Background

Molecules that selectively bind to nucleic acids have a large variety of uses, including serving as indicators for the presence or absence of a specific nucleic acid in a sample, as well as being used to modify gene regulation and/or protein expression.

One example of an indicator role is in the technique of in situ hybridization, which allows for the detailed spatial and temporal mapping of nucleic acid sequences, such as mRNAs, in normal and pathological tissues. In situ hybridization can be used to study gene expression and regulation in a morphological context from the sub-cellular to the organismal levels.

Methods for regulating protein expression, including RNA interference (RNAi) and anti-sense, not only have great therapeutic potential, but also provide critical tools for biologists working to infer regulatory relationships from the phenotypes resulting from the knockdown of specific genes. RNA interference can be activated by exogenous small interfering RNAs (siRNAs) or short hairpin RNAs (shRNAs) that work in concert with endogenous protein enzymes to cleave and degrade the targeted mRNA transcript. By contrast, antisense methods employ base-pairing between an exogenous antisense RNA and the target mRNA transcript to downregulate translation via RNase H activation or steric interference. Both techniques are powerful and widely used but have significant limitations. Effectiveness and specificity vary significantly from one target sequence to another.

In some situations, one fundamental conceptual weakness shared by current methods utilizing nucleic acid binding molecules is the reliance on base pairing to provide both sequence specificity and binding affinity. In in situ hybridization methods, increasing the probe length to improve binding affinity for cognate targets (reducing false negatives during the wash step) simultaneously increases the opportunity for partial base-pairing to non-cognate targets (increasing false positives). In RNAi, the recognition site is fixed at approximately 21 base pairs, leading to variable effectiveness and specificity depending on the degree of competing native secondary structure in the mRNA, the degree of partial complementarity to non-cognate targets, and other unknown factors. In anti-sense, increasing the length of the recognition site improves affinity for the cognate target but also increases the likelihood of base-pairing to non-cognate targets.

SUMMARY OF THE INVENTION

In some aspects, cross-linking probes are provided. In some embodiments, cross-linking probes comprise a nucleic acid initiator region, a nucleic acid probe region linked to the initiator region and a nucleic acid blocking region that is hybridized to the probe region. The initiator region is able to bind to a first portion of a target nucleic acid (when it is not blocked by the blocking region) and the probe region is able to bind to a second portion of the target nucleic acid. The first and second portions of the target nucleic acid may be contiguous. In some embodiments the probe additionally comprises a loop region that links the probe region to the blocking region. The initiator region may be, for example, a sticky end.

In some embodiments the initiator region is complementary to or substantially complementary to the first region of the target nucleic acid. In some embodiments the probe region is complementary to or substantially complementary to the second region of the target nucleic acid. In some embodiments the initiator region comprises one, two or three nucleotides that are not able to bind to the first portion of the target nucleic acid. In some embodiments the probe region comprises one, two or three nucleotides that are not able to bind to the second portion of the target nucleic acid.

One or more cross-linkers are part of the probe region. In some embodiments the probe region comprises two or more cross-linkers. The cross-linkers may be activatable, such as a light activatable or conformationally activatable cross-linkers. In some embodiments at least one cross-linker is selected from 4-Thio-dT and CNV-K. In some embodiments the cross-linker is internal to the terminal nucleic acids of the probe region. For example, in some embodiments there is at least one nucleotide of the probe region on each side of the cross-linker.

In some embodiments the cross-linking probe comprises a detectable marker, such as a fluorescent label.

In another aspect, methods of covalently cross-linking a cross-linking probe to a target nucleic acid sequence are provided. In some embodiments a target nucleic acid sequence in a sample is contacted with a cross-linking probe. The cross-linking probe may comprise an initiator region that is able to bind to a first portion of the target nucleic acid, a probe region that is linked to the initiator region and that is able to bind to a second portion of the target nucleic acid, one or more cross-linkers in the probe region and a blocking region hybridized to the probe region. When the cross-linking probe encounters the target nucleic acid, the initiator region and probe region bind to the first and second portions of the target nucleic acid sequence such that the blocking region dehybridizes from the probe region. The cross-linker may then be crosslinked to the target nucleic acid.

In some embodiments the initiator region is complementary to or substantially complementary to the first region of the target nucleic acid. In some embodiments the probe region is complementary to or substantially complementary to the second region of the target nucleic acid.

In some embodiments the cross-linker is activatable and cross-linking comprises activating the cross-linker. For example, the cross-linker may be photoactivatable and cross-linking may comprise exposing the sample to light. In some embodiments the cross-linker comprises one of 4-Thio-dT and CNV-K In another aspect, methods of disrupting the activity of a target nucleic acid by covalently cross-linking a cross-linking probe to the nucleic acid are provided. For example, the normal activity of a DNA, mRNA, miRNA, siRNA, tRNA, rTNA or piRNA may be disrupted by covalently binding a cross-linking probe. In some embodiments, translation of an mRNA is reduced. In general, a sample containing the target nucleic acid is contacted with a cross-linking probe, where the cross-linking probe comprises a nucleic acid initiator region, a nucleic acid probe region that is linked to the initiator region and comprises one or more cross-linkers and a blocking region that is hybridized to the probe region. The probe region may be linked directly to the initiator region. The initiator region is able to bind to a first portion of the target nucleic acid, and may, for example, be substantially complementary to the first portion of the target nucleic acid. The nucleic acid probe region is able to bind to, and may be substantially complementary to, a second portion of the target nucleic acid. In some embodiments the first portion of the target nucleic acid is contiguous with the second portion.

The initiator region and the probe region bind to the first and second portions of the target nucleic acid, such as by hybridization, and the blocking region is dehybridized from the probe region. After the probe region has bound to the target, the cross-linker(s) in the probe region are cross-linked to the target nucleic acid, thus covalently bonding the probe to the target. The bound probe disrupts the normal activity of the nucleic acid target. In the case of an mRNA target, cross-linking of the cross-linker to the target reduces translation of the target mRNA into protein.

In some embodiments, the target nucleic acid is an mRNA associated with a disease or disorder. In some embodiments, expression of protein from the target mRNA is associated with the disease or disorder and reduced expression may treat the disease or disorder. In some embodiments the target mRNA is a housekeeping gene mRNA, such as from a virus or bacterium.

In some embodiments, methods of silencing or reducing expression of a target gene are provided. A cross-linking probe comprising one or more cross-linkers is hybridized to a silencing-target nucleic acid, such as to an mRNA transcribed from the gene. The cross-linkers are crosslinked, thus covalently bonding the probe to the target nucleic acid and reducing or eliminating expression of the gene.

In some embodiments the probe used to silence or reduce expression of a target gene may comprise a nucleic acid probe region that is able to bind to a portion of the silencing-target nucleic acid, a blocking region that is hybridized to the probe region and at least one cross-linker that is part of the probe region. Upon contacting the target nucleic acid, the probe region hybridizes to the portion of the target nucleic acid such that the blocking region dehybridizes from the probe region. The cross-linker is then cross-linked to the target nucleic acid such that the probe is covalently attached to the target and redueces or silences expression of the target gene.

In other embodiments, methods of treating a disease or disorder are provided. A target nucleic acid is identified that is associated with the disease or disorder. For example, in some embodiments, the target nucleic acid is an mRNA where the expression of protein from the mRNA is associated with the disease or disorder. In other embodiments the target nucleic acid is a nucleic acid that is necessary for the survival of a pathogenic organism associated with the disease or disorder.

A cross-linking probe is provided to a patient suffering from the disease or disorder. The probe may be, in some embodiments, provided systemically. In other embodiments the probe is provided more locally to areas where the target nucleic acid is known or suspected to be located. For example, if the target is a nucleic acid associated with a pathogenic organism, the cross-linking probe may be provided to an area of infection with the pathogenic organism.

In some embodiments, the cross-linking probe comprises an initiator region that is able to bind, such as by hybridization, to a first portion of the target nucleic acid associated with the disease or disorder. The cross-linking probe may also comprise a nucleic acid probe region linked to the initiator region. The probe region is able to bind to a second portion of the target nucleic acid, such as by hybridization. In some embodiments the initiator region and probe region are complementary to the first and second portions of the target nucleic acid, respectively. The first and second portions of the target nucleic acid may be contiguous.

The cross-linking probe also comprises one or more cross-linkers within the probe region and a blocking region that is hybridized to the probe region. The blocking region and the probe region may be linked such as with a loop region.

When the probe contacts the target nucleic acid, the initiator region and the probe region bind to the first and second portions of the target nucleic acid and the blocking region dehybridizes from the probe region. The cross-linker within the probe region can then be cross-linked to the target nucleic acid, thereby covalently binding the probe to the target.

In other embodiments kits for covalently binding a cross-linking probe to a nucleic acid target are provided. The kits may comprise a cross-linking probe that is able to be cross-linked to a nucleic acid target. In some embodiments the nucleic acid target is associated with a disease or disorder. The kits may comprise other components, such as a carrier that facilitates introduction of the cross-linking probe into a cell. In some embodiments the cross-linking probe comprises an activatable cross-linker and the kits may comprises a component that can be used to activate the cross-linker upon binding of the cross-linking probe to the target nucleic acid. In some embodiments the cross-linking probe may comprise one or more detection molecules and the kits may comprise one or more components that can be used to visualize the cross-linking probe after it is covalently bound to the target nucleic acid. In still other embodiments, the kits may comprise components for washing unbound cross-linking probe from a sample.

DETAILED DESCRIPTION OF THE PREFERRED EMBODIMENT

Figure 1A:
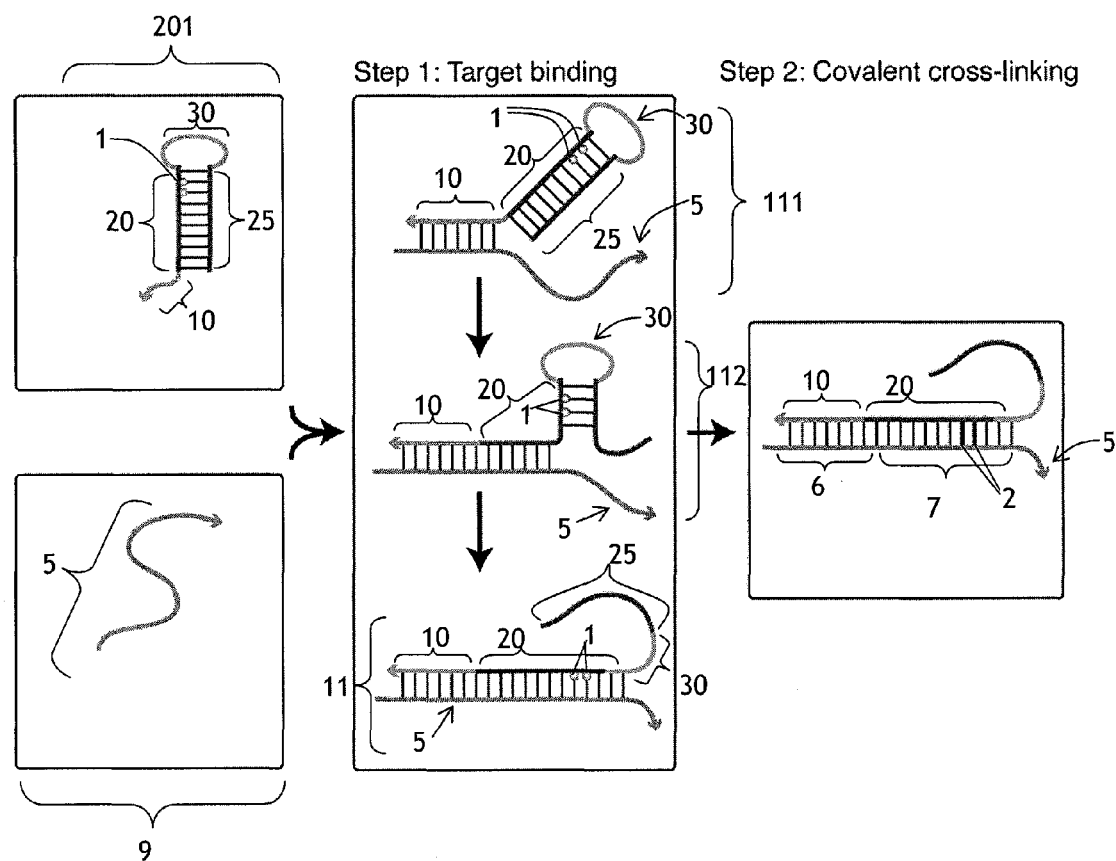
FIG. 1A depicts some embodiments of a cross-linking probe.

Triggered covalent probes as described herein can be used to target nucleic acid sequences with specificity. The probes typically comprise activatable nucleic acid cross-linkers. In some embodiments, the use of triggered covalent probes allows one to avoid or reduce the tradeoff between affinity and specificity that is common in current efforts to target nucleic acids. Some triggered probes and methods for their use are described in U.S. Ser. No. 12/467,755, filed May 18, 2009, which is incorporated by reference herein.

A wide variety of alternative cross-linking probes and various methods of using them are provided. In some embodiments, these probes and techniques provide the ability to create covalent bonds to their target nucleic acid and to do so with a high degree of selectivity and/or specificity. In some embodiments, these probes and techniques allow for the selective cross-linking of the probe to a specific nucleic acid. In some embodiments, the cross-linking itself is selective in that cross-linking between unbound cross-linking probes and non-target (and non-probe) nucleic acids is significantly reduced or prevented. However the selectivity and/or specificity need not be due to the crosslinks formed, but may be provided by the rest of the probe itself.

In some embodiments, molecular conformation change can be used to provide the specificity with which covalent links are formed between specifically bound probes and target nucleic acids, such as mRNAs. The covalent crosslinks can then provide affinity for the target independent of any base-pairing (allowing, for example, ultra-stringent washes for imaging applications or effective inhibition of translation for silencing applications).

In some embodiments, covalent cross-linking of a probe to a target nucleic acid sequence progresses sequentially. First, when the probe contacts the target, branch migration occurs, providing sequence specificity and placing the activatable cross-linkers in the probe in position to cross-link to the cognate target (e.g., mRNA). Second, activation of the cross-linkers yields covalent links to the target. As discussed below, in some embodiments the cross-linkers are externally activated, such as by providing light for photoactiatable cross linkers. In other embodiments the cross-linkers are intrinsically active and form cross-links when they come into contact with their target. In some embodiments, cross-linking preferably occurs if and only if the probe is base-paired to the cognate target. In some embodiments, the specificity provided by the branch-migration and the affinity provided by covalent cross-linking enable ultra-stringent washing to remove unbound probe. In other embodiments, such as some therapeutic embodiments, cross-linkers in unbound probes are activated, causing the probe to cross-link to itself and rendering it inert.

Triggered covalent probes find use in a wide variety of application. In some embodiments triggered covalent probes can be used for detecting the presence of a target nucleic acid in a sample, such as for in situ hybridization. For example, triggered covalent probes can be used in situ to provide quantitative imaging based on total fluorescence in fixed cells, embryos or other samples.

In some embodiments triggered covalent probes can be used in hybridization assays, such as chip-based hybridization assays, to identify the presence of particular nucleic acids with high specificity.

In some embodiments, triggered covalent probes can be used to disrupt genetic processes, such as for reducing gene expression or for gene silencing. In some embodiments, triggered covalent probes can be used therapeutically. As discussed further below, triggered covalent probes can be used in vitro and in vivo. Triggered probes can be used in any species, including bacteria and viruses, and as such in some embodiments can be used as an antibiotic or antiviral for therapeutic purposes.

Definitions

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention.

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques of described herein are those well known and commonly used in the art.

As utilized in accordance with the embodiments provided herein, the following terms, unless otherwise indicated, shall be understood to have the following meanings:

The term "nucleic acid" refers to natural nucleic acids, artificial nucleic acids, non-natural nucleic acid, orthogonal nucleotides, analogs thereof, or combinations thereof. Nucleic acids may also include analogs of DNA or RNA having modifications to either the bases or the backbone. For example, nucleic acid, as used herein, includes the use of peptide nucleic acids (PNA). The term "nucleic acids" also includes chimeric molecules.

As used herein, the terms "polynucleotide," "oligonucleotide," and "nucleic acid oligomers" are used interchangeably and mean single-stranded and double-stranded polymers of nucleic acids, including, but not limited to, 2'-deoxyribonucleotides (nucleic acid) and ribonucleotides (RNA) linked by internucleotide phosphodiester bond linkages, e.g. 3'-5' and 2'-5', inverted linkages, e.g. 3'-3' and 5'-5', branched structures, or analog nucleic acids. Polynucleotides have associated counter ions, such as $H^+$, $NH_4^+$, trialkylammonium, $Mg^{2+}$, $Na^+$ and the like. A polynucleotide can be composed entirely of deoxyribonucleotides, entirely of ribonucleotides, or chimeric mixtures thereof. Polynucleotides can be comprised of nucleobase and sugar analogs. Polynucleotides typically range in size from a few monomeric units, e.g. 5-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine.

The term "hairpin" refers to a structure formed by intramolecular base pairing in a single-stranded polynucleotide ending in an unpaired loop. A "hairpin loop" refers to a single stranded region that loops back on itself and is closed by a single base pair.

The term "initiator region" denotes a section of a probe that can bind to a target nucleic acid, or at least a first portion of the target nucleic acid. In some embodiments, the initiator region is generally two to 1000 nucleotides, such as 3-100 nucleotides or 4-50 nucleotides. In some embodiments, there can be more than one initiator. For example, in some embodiments there can be two initiators, one on each side of the probe region. In some embodiments an initiator region is substantially or completely complementary to a portion of a target nucleic acid. In some embodiments an initiator region comprises one, two, three or more nucleotides that are not able to bind to the corresponding target nucleic acids, such as mismatches relative to the corresponding portion of the target nucleic acid. However, the initiator as a whole retains the ability to bind to the target nucleic acid. In some embodiments an initiator region comprises less than three mismatches relative to a portion of a target nucleic acid. In some embodiments the initiator region is able to bind to a target nucleic acid sufficiently to facilitate binding of the probe region to the target nucleic acid and dehybridization of the blocking region.

The term "probe region" denotes a section of a hybridization probe that can bind to a portion of a target nucleic acid. In some embodiments, this is distinguishable from the initiator region in that an initiator region, if present, will bind to the target first. In some embodiments the initiator region binds to a first region of the target nucleic acid and the probe region binds to a second region of the target nucleic acid. In some embodiments these first and second regions of the target nucleic acid are contiguous. This initial binding of the initiator region allows for the initiation of the displacement, or dehybridization, of a blocking region that is hybridized to at least a portion of the probe region via a branch migration process. In some embodiments the probe region is 3-1000 nucleotides in length, such as 6-100 or 10-50 nucleotides in length. In some embodiments the probe region is substantially or completely complementary to a portion of a target nucleic acid. In some embodiments the probe region is not perfectly complementary and comprises one, two, three or more nucleotides that can not bind to the corresponding nucleotides of the target. However, the probe region as a whole retains the ability to bind to the target. For example, the probe region may comprise one, two, three or more mismatches relative to the portion of the target sequence to which it can hybridize. In some embodiments the probe region comprises less than three mismatches relative to the portion of the target sequence to which it can bind. In some embodiments the probe region is able to bind to a target nucleic acid sufficiently to allow cross-linking of the probe to the target nucleic acid.

The term "linked" or "links" denotes that two regions are covalently connected to one another. There can be additional intervening structures between the two regions. Thus, the linking can be direct (also described as being "immediately adjacent") or indirect. While two nucleic acids that become cross-linked could be characterized as "linked," for the sake of clarity, such links are referred to herein as "cross-links" and not generally denoted by the term "link". Thus, a single nucleic acid that includes a probe region, a cross-linker, a loop region, and a blocking region would all be "linked" to each other, and if the cross-linker cross-linked to the blocking region, then the cross-linker (and the probe region that the cross-linker is in) would be "cross-linked" to the blocking region.

The term "associated" denotes that the relevant structures and/or regions are localized with one another by some type of binding interaction. Association can be due to covalent bonds (e.g., linked or cross-linked) or they can be due to noncovalent bonds (e.g., hybridization, antibody binding, etc.)

The term "cross-linked" denotes that a cross-linker has formed a covalent bond with another residue, molecule, nucleotide, etc. The bond can be formed within the same molecule (e.g., cross-linking a hairpin loop shut) or can be between molecules (e.g., cross-linking a cross-linking probe to a target molecule). "Cross-linked" can include one or more cross-linked bonds.

The term "cross-linker" denotes a molecule or atom that is capable of forming a covalent bond to another molecule. "Cross-linker" does not encompass molecules that are only able to form Watson-Crick type interactions; rather, cross-linkers must be able to form a covalent bond to another molecule. While the cross-linkers should allow for two separate molecules (e.g., nucleic acids) to be effectively cross-linked together, more than one cross-linker can be used, thus, any single cross-linker does not need to be strong enough to keep the two molecules bonded together. In some embodiments more than 1, 2, 3, 4, 5, 6, 7, 8, 9, 10, 11, 12, 13, 14, 15 or 20 cross-linkers are present in any particular cross-linking probe. The cross-linkers may all be the same, or may comprise two or more different types of cross-linkers. In some embodiments, the cross-linker is capable of forming a covalent bond between the target nucleic acid and a probe region.

The term "blocking region" denotes a structure that obstructs the probe region and cross-linker when it is hybridized to the probe region. While the blocking region need not completely prevent any interaction of the cross-linker and/or probe region with the environment, it will significantly reduce this interaction so as to allow a greater degree of specificity of cross-linking that will depend upon the presence or absence of the blocking region. The blocking region is displaced (de-hybridized) via a branch migration in which base-pairs between the probe region and blocking region are replaced one at a time by base pairs between the probe region and the target. Hence, the cross-linkers are shielded (and in some embodiments are always effectively shielded) from the biological sample either within the probe or between the probe and the intended target. In some embodiments, the blocking region contains one or more areas that are inert to cross-linking. For example, the blocking region can contain a sub-region that is just the polymer backbone without any bases. The blocking region can be a single strand of nucleotides or one or more strands of nucleotides.

The term "reversibly hybridize" denotes that the molecule can hybridize and dehybridized (dissociate or be displaced from) from a nucleic acid. Nucleic acids that are cross-linked to one another will not dissociate due to the covalent interaction. However, molecules that include cross-linkers that have not been activated can still reversibly hybridize or dissociate from a complementary molecule. In addition, a molecule can be described as being "reversibly hybridizable," even if it has a cross-linker in it, as long as it can dissociate from a binding molecule.

The term "reduce" denotes some decrease in amount. In some embodiments, an event is reduced by 1, 2, 3, 4, 5, 10, 15, 20, 25, 30, 35, 40, 45, 50, 55, 60, 65, 70, 75, 80, 85, 90, 95, 96, 97, 98, 99, 99.9, 99.99, 99.999, 99.9999, 99.99999, 99.999999, 99.9999999 percent or more, including any value above any of the preceding values, as well as any range defined between any two of the preceding values.

The term "loop region" denotes a region that links a probe region and a blocking region. This region is optional. The loop region can include nucleotides and/or simply be a polymer backbone without any bases.

The modifier "sub" denotes a component of a region.

The term "detectable marker" denotes any molecules that can be observed and/or detected, either directly (e.g., fluorescence), or indirectly (e.g., detection of a product, where the presence of the product is based upon the presence of a target). For indirect detectable markers, the molecule that acts as the intermediate can be the "detectable marker," even if it is a product from that molecule that is actually detected. In some embodiments, a detectable marker is a part of the probe that can serve as a marker, such as in a surface plasmon resonance technique (such as in a BIACORE™ machine). Thus, in some embodiments, no separate detectable marker need be included.

The term "amplifier molecule" denotes a molecule that allows for the association of a detectable marker with a probe region. This association can be indirect, e.g., through an additional pairing region. The amplifier can be cross-linked to the cross-linking probe, but need not be.

The term "pairing region" denotes a nucleic acid sequence that can hybridize to a complementary pairing region.

The term "complementary pairing region" denotes a nucleic acid sequence that can hybridize to a pairing region.

The term "orthogonal nucleotides" denotes nucleotides other than natural nucleotides. Natural nucleotides are defined as adenine, cytosine, guanine, thymine, and uracil and their deoxyribonucleotide analogs. Some types of orthogonal nucleotides contain modified bases, such as isoC and isoG.

The term "external linker" denotes one or more atoms that serve to link two molecules together. A cross-linker can be attached to or include an external linker, which can allow for greater flexibility in the positioning of the cross-linker. The term "external" is used to further distinguish this linking aspect from a cross-linker (which is capable of forming a cross-link), as an external linker need not be capable of actually forming a cross-link after it has been connected and can merely serve as a longer tether to attach, for example, the cross-linker to the probe region.

The term "activated" denotes that the cross-linker is in a state to cross-link a target.

The term "activatable" denotes that a cross-linker has a state dependent ability to cross-link. In some embodiments, the "state" is an environmental factor, such as radiation (UV, visible, etc.) or the presence of a particular chemical compound. In other embodiments the state is a particular conformation and the cross-linker can be activated by a conformational change (such as the presence of absence of the blocker region hybridized to the probe region).

The term "unactivated" denotes that an activatable cross-linker has not been activated, and thus, the likelihood that a cross-link will be formed is very low.

The term "un-cross-linked" denotes that the cross-linker has not been cross-linked. A molecule can be activated and still be uncross-linked.

The term "ultrastringent wash" denotes a washing condition that is much more effective at weakening hybridization interactions than those commonly used for in situ hybridization. Examples include elevated temperatures and high concentrations of chemical denaturants such as formamide, organic cosolvents, or urea. In some embodiments, an ultrastringent wash would completely eliminate nucleic acid hybridization in the sample, thus causing any non-crosslinked probes to dissociate from their binding sites. In some embodiments, an ultrastringent wash would typically be one that is strong enough to destabilize all base-pairing (including orthogonal base pairs) between the probe and the sample. This could be achieved using higher temperatures or (e.g. high concentration of formamide). In some embodiments, an ultrastringent wash comprises 2×SSC and 75% formamide at 70 degrees. In some embodiments, 20-50% formamide is employed instead of 75%. In some embodiments, these wash conditions are for relatively short probes of less than 1000 nucleotides, for example, 900, 800, 700, 600, 500, 400, 300, 200, 100, 50, 40, 30, 20, 10 or fewer nucleotides, including any range defined between any two of the preceding values.

The term "target nucleic acid" denotes a nucleic acid of interest. In some embodiments, the target nucleic acid is one that a user wishes to determine the presence or absence of. In some embodiments the target nucleic acid is associated with a disease or disorder. In some embodiments the target nucleic acid is associated with a pathogenic organism. In some embodiments the target nucleic acid is one whose expression is necessary for the survival and/or reproduction of an organism, such as a pathogenic organism. In some embodiments the target nucleic acid is related to a gene that a user wishes to reduce or silence expression from. In some embodiments, the target nucleic acid is one that the user may wish to specifically attach a cross-linker to. Exemplary target nucleic acids include DNA, RNA, mRNA, miRNA, siRNA, tRNA and piRNA. In some embodiments a target nucleic acid is endogenously expressed in a cell. In some embodiments a target nucleic acid is foreign to a host cell or organism. In some embodiments target nucleic acids may be, for example, viral nucleic acids or bacterial nucleic acids.

The term "cross-linking probe" denotes a molecule that is capable of selectively binding to a target nucleic acid and then cross-linking to that nucleic acid. While cross-linking probes can be used to "probe" for the presence of specific target nucleic acids in a sample, a "cross-linking probe" is not limited to this use and need not include a detectable marker or other detectable aspect. For example, a cross-linking probe can include only a nucleic acid probe region and a cross-linker. Such a probe can be used to obstruct or inactivate a target nucleic acid, rather than for the detection of the presence or absence of the nucleic acid. Of course, the probes can include the other aspects disclosed herein as well.

As used herein, "treatment" is a clinical intervention made in response to a disease, disorder or physiological condition manifested by a patient or to be prevented in a patient. The aim of treatment includes the alleviation and/or prevention of symptoms, as well as slowing, stopping or reversing the progression of a disease, disorder, or condition. "Treatment" refers to both therapeutic treatment and prophylactic or preventative measures. Those in need of treatment include those already affected by a disease or disorder or undesired physiological condition as well as those in which the disease or disorder or undesired physiological condition is to be prevented. "Treatment" need not completely eliminate a disease, nor need it completely prevent a subject from catching the disease or disorder.

A "subject" or "patient" is any animal, preferably a mammal, that is in need of treatment.

Cross-linking Probes

In some embodiments, a shielded cross-linking probe includes a nucleic acid initiator region, a nucleic acid probe region, one or more cross-linkers that are in or part of the probe region, and a blocking region that reduces the ability of the cross-linker to cross-link and/or the probe region to bind to undesired sequences. The blocking region may be hybridized to the probe region to form a duplex region in the absence of target and, in some embodiments, is substantially or completely complementary to some or all of the probe region. The blocking region will dehybridize from the probe region in the presence of the target nucleic acid, which then allows the target nucleic acid to interact with the probe region and the cross-linker to cross-link to the desired target. In some embodiments, the cross-linker is intrinsically active and/or is activated simply by the dehybridization of the blocking region. In other embodiments, the selectivity of the cross-linker is enhanced further by the use of an externally activatable cross-linker, which allows one to determine when and/or where in a reaction, sample, or system the cross-linker should become capable of cross-linking. The above selective cross-linking can provide a variety of useful functions. For example, the specifically cross-linked probe can be used in an in situ hybridization technique which can then employ ultra-stringent washing conditions in order to improve in situ results. Other examples, such as gene silencing and treatment of diseases and disorders are described herein. Of course, any process in which very specific and very tight (e.g., covalent level strength) binding between a molecule and a target nucleic acid are beneficial can benefit from one or more of the embodiments disclosed herein.

The initiator region allows for the initial priming of the cross-linking probe to the target nucleic acid and can allow for subsequent strand displacement of the blocking region. This is not required for all embodiments. In some embodiments the initiator region is at least 2 and typically not more than 200, but can be as many as 1000 nucleotides or more. In some embodiments, the initiator is immediately adjacent to the probe region. In some embodiments there can be an intervening structure, as long as effectively specific strand displacement is maintained.

The probe region ensures that the molecule that the cross-linker cross-links to is the specific nucleic acid that is desired. The probe region can be a single continuous nucleic acid or it can be broken into two or more parts. In some embodiments, the probe region will include 3-50 nucleotides. In some embodiments, the probe region is less than 300 nucleotides. In some embodiments, the probe region is less than 200 nucleotides. In some embodiments, the probe region is less than 100 nucleotides. In some embodiments, the probe region is extended into the loop to further lock the probe in the open conformation once it is bound specifically to the target nucleic acid.

In some embodiments, one or more cross-linkers are associated with the probe region. In some embodiments, at least two cross-linkers are associated with the probe region. Each of the cross-linkers may be the same in a given probe, or the probe may comprise more than one type of cross-linker.

In some embodiments, a cross-linker is located on one of the terminal nucleotides of the probe region. The terminal nucleotides of the probe region are the nucleotides at the 5' and 3' ends of the probe region. In some embodiments the terminal nucleotides at the 5' and 3' ends of the probe region are the first and last nucleotides of the probe region that are associated with the blocking region. In some embodiments, however, a cross-linker within the probe region is not located at a terminal nucleotide of the probe region. Rather, one or more cross-linkers may be, for example, 1, 2, 3, 4, 5, 6, 7, 8, 9, 10 or more nucleotides in from one or both terminal nucleotides of the probe region. In some embodiments one or more cross-linkers are located 1, 2, 3, 4, 5, 6, 7, 8, 9, 10 or more nucleotides in from the first and/or last nucleotides of the probe region that are associated with the blocking region.

In some embodiments, the probe region comprises at least one nucleotide on both sides of one or more cross-linkers. When two or more cross-linker molecules are present, each cross-linker may be associated with adjacent nucleotides, or the cross linkers may be separated by 1, 2, 3, 4, 5, 6, 7, 8, 9, 10 or more nucleotides. When more than two cross-linkers are present, they may be spaced regularly, such as every two nucleotides, or with variable spacing between them.

As noted above, not all cross-linking probes require activatable cross-linkers, loop regions, and/or initiator regions. In some embodiments, the cross-linking probe includes a probe region, one or more cross-linkers, and a blocking region, that reduces the accessibility of the cross-linker to external nucleic acids. In some embodiments, the cross-linking probe further includes an initiator region. In some embodiments the initiator region is immediately adjacent and linked to the probe region such that binding of a target to the initiator region allows for strand displacement of a molecule hybridized to the probe region (e.g., the blocking region). In some embodiments, the cross-linking probe further comprises a loop region that links the probe region and the blocking region. In some embodiments, the cross-linking probe further comprises a detectable marker. In some embodiments, the cross-linking probe comprises a detectable marker region. In some embodiments, the cross-linking probe comprises a pairing region. The pairing region can be linked to the blocking region or can be linked to the probe region or loop region. In some embodiments, the pairing region can be or be part of the looped region (and thus will be accessible for hybridization upon displacement of the blocking region and the probe region.

In some embodiments, the blocking region is the same length as the probe region. In some embodiments, the blocking region is shorter than the probe region, but long enough to effectively reduce or inhibit non-target based cross-linking. In some embodiments the blocking region covers the first and last activatable cross-linkers in the probe region. In some embodiments, the blocking region comprises one or more nucleic acid strands and thus, comprises multiple subparts. In some embodiments, the blocking region has orthogonal bases. In some embodiments a part of the blocking region (e.g., the portion that might otherwise be at risk of cross-linking with the cross-linker) lacks those atoms or residues that allow for cross-linking. For example, in some embodiments, the blocking region only includes a backbone at those sections and lacks a base for cross-linking to. In some embodiments, the blocking region at those sections is such that it does not base pair with the corresponding portion of the probe region.

In some embodiments, the probe region and the blocking region are connected by a loop region. The loop region can include one or more nonnatural nucleotides or orthogonal nucleotides. In some embodiments, the loop region is a linker or polymer and need not be nucleotide based, as long as it can link the probe region and the blocking region. In some embodiments, the loop includes nucleotides that can bind to the target nucleic acid, thereby further enhancing the hybridization.

In some embodiments, to avoid off-target effects associated with traditional antisense regulation, the initiator region or toehold can be made too short to function as an antisense strand if it base-pairs non-specifically in the sample. Chemical modifications can also be used to minimize non-specific digestion by nucleases in the cell.

As will be appreciated by one of skill in the art, the cross-linking probe and its use can be employed for any target nucleic acid, such as those nucleic acids that one may wish to observe (such as in in situ hybridization) or those that one may target for covalent modification (which would naturally impair the functionality of that nucleic acid), such as an mRNA associated with a gene whose expression is desired to be reduced or silenced. Exemplary target nucleic acids may include, for example: RNA, DNA, mRNA, miRNA, rRNA, tRNA, miRNA and piRNA. The target nucleic acids can be from any organism, including, but not limited to, mammals, mice, rats, primates, humans, etc. In some embodiments, the target nucleic acid remains in the host cell or subject. Thus, in some embodiments, the method can be performed in vivo, ex vivo, or in vitro. In some embodiments, the method is performed in a cell. In some embodiments, the method is performed in tissue. In some embodiments, the tissue is in a living host.

In some embodiments, shielded cross-linking probes will form a crosslink to a target (such as mRNA) with high specificity by employing one or more of the following: 1) initial sequestration of one or more activatable or intrinsically active cross-linkers within a duplex portion of a nucleic acid probe; 2) stringent sequence filtering via competitive branch migration replacement of blocker/probe region base pairs with probe/target base pairs such that upon completion of the triggered conformation change, the cross-linkers are sequestered within a new probe/target duplex; and 3) high-yield activation of the cross-linkers. These properties, especially when more than one is present, will ensure that the probe covalently cross-links to the sample primarily (and in some embodiments only) when it is specifically base-paired to its complementary target.

In some embodiments, a cross-linking probe with a hairpin structure binds to a target nucleic acid via the following sequence of events: nucleation, branch migration and full-base pairing. In the nucleation step, an exposed single-stranded initiator region, often a single-stranded toehold such as a sticky end, promotes nucleation with the complementary target nucleic acid sequence via base-pairing. Following nucleation, probes that are bound to the cognate target begin a branch migration in which base pairs within the duplex region of the hairpin probe are replaced one by one with probe/target base pairs, such that the probe region comprising one or more cross-linkers hybridizes to the target. Mismatches produce an energetic barrier to further migration and thus the probe duplex acts as a tunable filter that can provide high specificity. In some embodiments, a single mismatch can significantly inhibit migration. In other embodiments, from 1-4 mismatches can significantly inhibit migration. As a result, given the appropriate probe configuration, bases of the probe carrying activatable cross-linkers can base-pair to exogenous nucleic acids if the probe is bound specifically to the target, in which case the cross-linkers are sequestered within a new probe/target duplex. Full base pairing is achieved and branch migration completed if the probe is bound specifically to its cognate target. In some embodiments the probe is a hairpin monomer and unfolding of the hairpin loop region can stabilize the probe/target complex. In other embodiments the cross-linking probe does not comprise a hairpin loop, and the strand of the duplex region that does not bind to the target is released upon completion of the branch migration.

Following branch migration, the cross-linker(s) can be activated (if necessary) to covalently bind the probe to the target. Activation can be carried out immediately, or delayed to a desired time. As discussed below, activation may take a variety of forms. In some embodiments photoactivatable cross-linkers are activated by exposing at least a portion of the sample to light. The particular wavelength of light will depend on the specific cross-linker and can be determined by the skilled artisan. Oxidation, reduction, or provision of activating chemicals may also be used, depending on the nature of the cross-linker. In other embodiments, cross-linking is activated simply by the change in conformation of the probe that occurs upon branch migration. In some embodiments, the entire sample is exposed to an activating agent. In other embodiments, only a portion of a sample is exposed to an activating agent. For example, in some therapeutic embodiments, a section of the body of a patient in which cross-linking of probe to target is desired may be specifically exposed to the activating agent, such as the appropriate wavelength of light.

In some embodiments, after cross-linking unbound cross-linking probe is washed away from the sample. In some embodiments, the washing conditions are more stringent than are used for situations in which a probe is simply hybridized to a target. Thus, the washing conditions can be higher than allowed for typical in situ washes. In some embodiments, unbound cross-linking probe is simply allowed to dilute away, without active washing.

In some embodiments, the amount of the cross-linking probe provided is sufficient to allow for the determination of the presence or absence of a target nucleic acid. In some embodiments, the amount of the cross-linking probe provided is sufficient to allow for the determination of the amount of a target nucleic acid. In some embodiments the amount of the cross-linking probe provided is sufficient to reduce expression from a target gene. In some embodiments the amount of cross-linking probe provided is sufficient to effectively silence expression from a target gene.

In some embodiments the amount of probe provided is approximately the same as the known or estimated amount of target. In other embodiments probe is provided at a 1.5:1, 2:1, 2.5:1, 3:1, 4:1, 5:1, 10:1 or higher ratio of probe to target. In some applications, the concentration of probe is higher than the concentration of the target (e.g., imaging rare mRNAs). In some applications, the probe concentration may be lower (e.g., detecting DNA or RNA on a chip).

In some embodiments, the amount of the cross-linking probe provided is sufficient to allow for binding and cross-linking to at least 1% of the target nucleic acid present in the sample to be exposed to the cross-linking probe, for example 1, 2, 3, 4, 5, 10, 15, 20, 25, 30, 35, 40, 45, 50, 55, 60, 65, 70, 75, 80, 85, 90, 95, 96, 97, 98, 99, 99.9, 99.99, 99.999, 99.9999, 99.99999 or greater percent of the nucleic acid target is cross-linked to a cross-linking probe, including any amount greater than any of the preceding values and any range defined between any two of the preceding values.

Orthogonal nucleotides can be used for a variety of purposes in a cross-linking probe or the molecules that are associated therewith. In some embodiments, these orthogonal nucleotides can be used to improve or ensure specificity between an amplifier molecule and a molecule that includes a probe region. In some embodiments, they can be used to provide for a blocking region that can block or obstruct a cross-linker, while preventing the cross-linker from forming a cross-link with the blocking region. In such an embodiment, any nucleotide that will not effectively cross-link with the cross-linker can be used. Indeed, in some embodiments, a molecule that only contains the backbone of the nucleotide and/or lacks one or more atoms involved in cross-linking (such as the bases) can be used.

The upper-left corner of FIG. 1A depicts an embodiment of a cross-linking probe. This cross-linking probe 201 comprises a single-stranded initiator region 10, which can also be referred to as an exposed, single-stranded toehold segment or a sticky end. The initiator region 10 is contiguous with and/or linked to a probe region 20. In some embodiments, the probe region 20 forms part of a duplex stem of a hairpin monomer. In the illustrated embodiment, the probe region 20 includes at least one cross-linker 1. In some embodiments one or more crosslinkers are located at one terminal end of the probe region 20.

In some embodiments, multiple single-stranded toeholds that are able to hybridize to the target nucleic acid may be separated by multiple probe and/or blocking regions, some or all of which may contain crosslinkers. Thus, in some embodiments, a cross-linking probe comprises a first initiator region or toehold, a first probe region that is hybridized to a first blocking region, a second toehold segment that is adjacent to the first probe region, and a second probe region that is adjacent to the second toehold segment and is hybridized to a second blocking region. In some embodiments, the first initiator region, first probe region, second toehold region and second probe region are able to hybridize to contiguous portions of a target nucleic acid. In some embodiments a third toehold segment, probe region and blocking region are included. Additional toehold segments, probe regions and blocking regions can be included. Each toehold segment and probe region are able to hybridize to contiguous portions of a target nucleic acid and each blocking region is able to hybridize to the relevant probe region. One or more of the probe regions comprise one or more cross-linkers.

Returning to FIG. 1, in the illustrated embodiment, cross-linker 1 and/or probe region 20 are/is initially obstructed from freely interacting with the environment (in particular, any part of the sample that is not the intended target sequence) by a blocking region 25 that is effectively complementary to the probe region 20 (complementary enough to allow this beneficial blocking to occur).

In the depicted embodiments, there is an optional loop region 30, which links the probe region 20 to the blocking region 25.

A target nucleic acid 5 is able to hybridize to the initiator region 10. In some embodiments, the target nucleic acid 5 comprises a sequence that is fully complementary to the initiator region 10 and the probe region 20.

As shown in FIG. 1A, combining a target nucleic acid 5 with the cross-linking probe 201 allows for the initiator region 10 to hybridize to the target sequence (depicted as process 111), which allows for branch migration up the cross-linking probe (depicted as process 112) and thus for the separation of the probe region 20 from the blocking region 25. This then allows for the base-pairing of both the initiator region 10 and the probe region 20 to the target nucleic acid 5 (depicted as process 11). Following this, in some embodiments, one can then activate the cross-linker(s) 1, such as via photo-activation. In other embodiments, the cross-linker is intrinsically activated, such as from a conformational change occurring upon separation of the probe region 20 from the blocking region 25. Activation of the cross-linker allows the cross-linker(s) 1 to form cross-link(s) 2 between the probe region 20 and the target nucleic acid 5 (in particular, the section of the target that is complementary to the probe region 7). In some embodiments, the initiator region is immediately adjacent to the probe region so as to promote effective strand displacement of the blocking region 25 upon binding of the initiator region 10 to target.

As noted above, a specific and tight association between a target and the probe can be beneficial in any technique where a relatively high degree of specificity and tight association is beneficial. In some embodiments, the cross-linking probes have the ability to discriminate targets from nucleic acids with a 1, 2, 3, 4 or greater nucleotide mismatch relative to the target sequence.

Figure 1B:
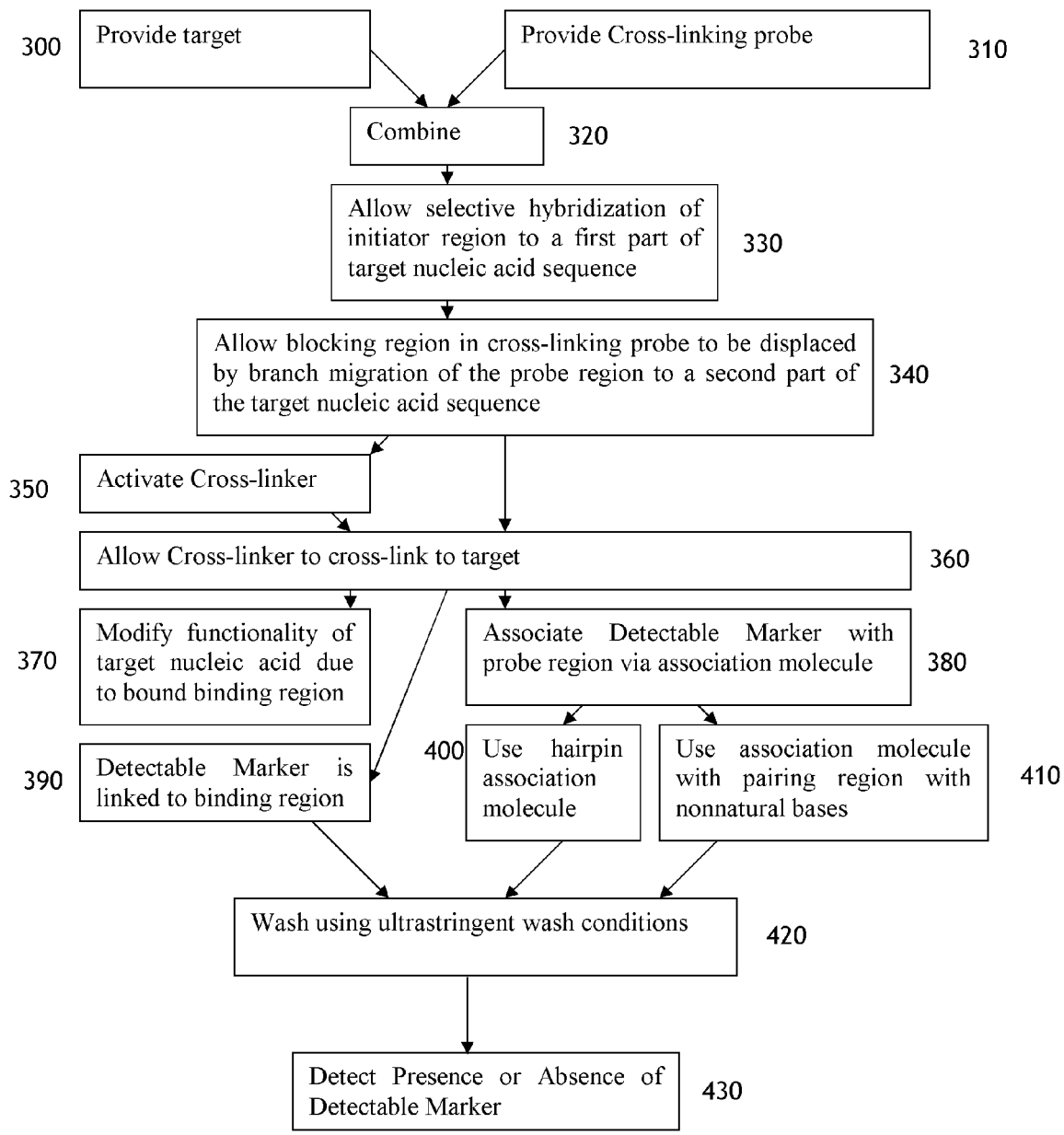
FIG. 1B is a flow chart outlining some embodiments of using a cross-linking probe.

FIG. 1B provides a flow chart outlining a variety of possible steps in various methods of using such a cross-linking probe. As shown in FIG. 1B, one can start by providing (e.g., making and/or obtaining) a target nucleic acid 300 (or a sample that is suspected of having a target nucleic acid), providing the cross-linking probe 310, and combining the two 320. One then allows (and/or promotes) the selective hybridization of the initiator region to at least a part of the target nucleic acid 330 and allows (and/or promotes) the selective hybridization of the probe region to a second part of the target nucleic acid sequence 340. In embodiments that employ an activatable cross-linker, one can then activate the cross-linker 350. One then allows the cross-linker to cross-link to the target 360. In some embodiments, this can achieve the result of modifying the functionality of the target nucleic acid 370. In some embodiments, e.g., when the probe is used for in situ type methods, it can be useful to have detectable markers associated with the probe region. In some embodiments, the detectable marker (and/or the detectable marker region) is already part of the cross-linking probe and can be linked, directly or indirectly to the probe region 390. In some embodiments, the detectable marker region is associated with the probe region via an amplifier molecule, in process 380. This can be achieved via a pairing region and a sequence that is complementary to the pairing region. In some embodiments, a hairpin structure is used as the amplifier molecule 400. In some embodiments, the pairing region and pairing region complement are paired via the use of orthogonal bases that do not hybridize with natural nucleic acids. 410. Once one or more detectable markers are associated with the probe region, the sample can be washed to remove any non-cross-linked probes. Following the wash, one can examine the sample for the presence or absence of the detectable marker to determine whether or not the target nucleic acid is present in the sample. Alternatively, in some embodiments if the probes are localized on a chip or other substrate, washes can be used to remove the portion of the sample that is not cross-linked to the probes. The chip or substrate can then be examined for the presence of the target nucleic acid. In some embodiments, given that the desired probe is cross-linked to the desired target, ultrastringent wash conditions can be used 420.

Cross-linking between the probe and the target can be achieved in a number of different ways, depending on the type of cross-linker utilized. In some embodiments, the cross-linking chemistries are non-promiscuous (i.e., cross-linking occurs only between strands that are base-paired to each other). Due to the specificity provided by the branch migration, only those probes that are base-paired specifically to target nucleic acids are cross-linked to the target. Other probes (not bound to target with specificity) are fused in the closed state, due to covalent linking of the blocking region and the probe region.

In some embodiments, the cross-linker is intrinsically active and will be able to cross link when it comes into contact with the target. In other embodiments the cross-linker is activated by addition of an external factor, such as light or a chemical. In some embodiments the cross-linker can be photo-activated. That is, one or more cross-linkers in the probe are activated at a single point in time by exposing the sample to light, such as UV light. In some embodiments a sample is selectively exposed to the external agent, such that probe is only cross-linked to the target in a desired portion of a sample, such as a subset of cells or tissue. In some embodiments, various sections of a single sample comprising target and cross-linking probe are activated at separate times. For example, various regions of a substrate comprising nucleic acids can be exposed to light at different times. In some embodiments, localized, selective activation may be accomplished by providing an activating agent to the area in which cross-linking of probe to target is desired. For example, light of the appropriate wavelength may be provided to a particular area of a sample through the use of a light probe. Similarly, in some therapeutic embodiments, photo-activatable cross-linkers may be activated to cross-link probe to a target nucleic acid in a particular tissue of a patient by exposing the tissue to light.

In other embodiments, cross-linking of probe to target is conformation activated. That is, in some embodiments cross-linkers are activated at different points in time as individual probe molecules complete their branch migration upon binding to specific target nucleic acids. The activation can be triggered by the change in the environment of the cross-linker (for example, due to a change from B-form DNA duplex in the probe to A-form DNA/RNA duplex in the probe/target complex, or due to a change from a Watson-Crick base pair in the probe duplex to a wobble base pair in the probe/target duplex). Conformational activation causes covalent cross-linking if and only if the probe is bound specifically to the target nucleic acid. Probes that are not base-paired to the cognate target do not activate their cross-linkers (or in some embodiments, this cross-linking occurs to a significantly lesser extent). In some embodiments, the blocking section of the probe is incapable of (or has a greatly reduced ability to) crosslink to the cross-linkers in the probe. For example, the blocking section may include a section that is the polymer backbone without components necessary for cross-linking with the cross-linker.

In some embodiments, covalent cross-linking of a probe to nucleic acid targets (such as DNA or RNA) within a fixed sample allows for the use of ultra-stringent washes capable of destabilizing all base pairs between the probe and the sample (specific or non-specific) so that the sample retains essentially only those probes that are covalently cross-linked to their target. If the probes are directly labeled with fluorophores, fluorescence microscopy can be used to achieve quantitative imaging of mRNA expression due to the exquisite specificity of the cross-linking and the stringency of the wash. If in situ amplification is desired, the probe can carry a recognition domain for amplification by a variety of methods prior to imaging. Other detectable labels that are known in the art can also be used. In some embodiments, the covalent cross-linking probes can be localized on a chip or substrate and used to determine whether a target nucleic acid is present in a sample that is exposed to the chip or substrate. The substrate may contain cross-linking probes that are specific to a single target, or a variety of different cross-linking probes such that the presence of multiple different targets in a sample may be determined. In other embodiments, nucleic acids from a sample can be localized on a substrate and contacted with one or more cross-linking probes to identify their presence and/or amount on the substrate.

In other embodiments, covalent cross-linking of the probe to target nucleic acids (e.g., RNA or DNA) can be used to prevent that nucleic acid from functioning in its typical way in a system. For example, covalent-cross linking of probe to a target mRNA can provide effective steric inhibition of translation. In other embodiments, covalent triggered probes can be used to inactivate small regulatory RNAs such as microRNAs. While cells possess limited capabilities for repairing DNA cross-linking (which is nonetheless extremely genotoxic), cells are not understood to have evolved endogenous machinery for removing covalent cross-links to RNA. Hence, triggered covalent probes can provide a synthetic gene silencing pathway with exquisite specificity, extreme effectiveness (e.g., nearly complete knockdown of gene expression), and the flexibility to be used in any species (because this synthetic gene silencing pathway does not require endogenous proteins that may be lacking in some species). In some embodiments, despite the DNA repairing machinery, crosslinking to DNA will also effectively inhibit gene expression.

In embodiments in which cross-linking of probe to target is used to disrupt the function of a nucleic acid, washing may not be required. Thus, in some such embodiments, washing is not carried out after contacting the target with the cross-linking probe or after cross-linking has occurred.

If desired, a triggered covalent probe molecule can be used for both silencing and imaging at different stages during a process (such as an experiment or a method of treatment).

Cross-Linkers

In some embodiments, one or more cross-linkers are used in a cross-linking probe. In some embodiments, the cross-linkers are activatable. In some embodiments, the activatable cross-linker is a photo-activatable cross-linker. In some embodiments, the photo-activatable cross-linker is activated by exposure to UV light. In some embodiments, any compound that forms interstrand cross-links when activated by ultraviolet light can be a photo-activatable cross-linker. In some embodiments, the photo-activatable cross-linker only cross-links when exposed to ultraviolet light, reducing the risk of premature cross-linking that could reduce probe sensitivity.

Exemplary photo-activatable cross-linkers include azo compounds (aryl azides, diazo esters and diazirines); benzophenones; furocoumarins (also called furanocoumarins), including psoralens and their derivatives, such as tremethylpsoralen, 8-methoxypsoralen and angelicin (Pieles, U. and Englisch, U. Nucleic Acids Research, 1989. 17: p. 285-299), thiols (Killops, K. L., Campos, L. M., Hawker, C. J. Journal of the American Chemical Society, 2008. 130: p. 5062-5064), and halogenated nucleobases (Willis, M. C., et al. Science, 1993. 262: p. 1255-1257). Photoactive nucleoside analogs are used in some embodiments, such as nucleosides derivatized with any of the above groups, halogen or sulfur-substituted nucleobases (e.g. thiouracil, 5-fluoro-4-thiouridine), and nucleoside analogs with vinyl substituents (e.g. p-carbamoyl phenol nucleoside, 3-cyanovinylcarbazole nucleoside).

In other embodiments, chemically-activated cross-linkers are utilized. These may include reductively-activated cross-liners, such as mitomycin, doxorubicin and related molecules, oxidatively activated cross-liners, such as cyclophosphamide, furan-derivatized nucleosides and nucleoside analogs and metal-activated cross-linkers, such as Cpyl.

In other embodiments, conformationally activated cross-linkers are used. These may also be referred to as intrinsically-active cross-linkers and form cross-links upon hybridization to the target without any need for external activation. Exemplary conformationally activated cross-linkers include, but are not limited to, alkylating electrophiles, such as alkyl halides, haloacetamides, nitrogen and sulfur mustards and nucleoside and nucleoside analogs functionalized with these groups; aziridine and other strained-ring cross linkers, including aziridine functionalized nucleosides and nucleoside analogs and cyclopropylpyrroloindolones (e.g. CC-1065 and duocarmycin); and nucleoside analogs with reactive vinyl groups, such as 2-amino-6-vinylpurine and its sulfur protected derivatives, as well as 4-amino-6-oxy-2-vinylpyrimidine and its derivatives.

The above cross-linker list is not an exhaustive list of all possible cross-linkers, but is merely representative of various types of cross-linkers.

In some embodiments, one or more cross-linkers, such as 5'-psoralen cross-linkers (FIG. 7), are positioned at a nick in the duplex stem of a triggered covalent probe or at the blunt duplex end of a loopless triggered covalent probe. Quantitative cross-linking yield using one or more internal cross-linkers will aid in providing quantitative puncta.

In some embodiments, one or more of the cross-linkers are different from the cross-linkers disclosed in U.S. Ser. No. 12/467,755.

Figure 8A:
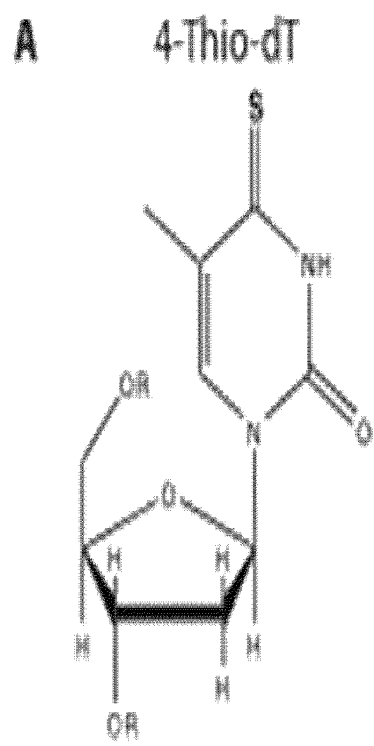
FIG. 8A is an illustration of the chemical structure of a 4-Thio-dT cross-linker used in some embodiments.
Figure 8B:
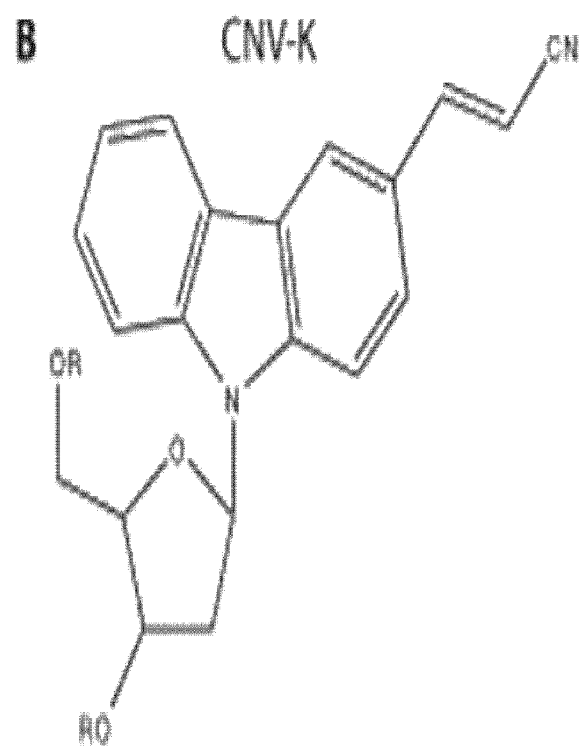
FIG. 8B is an illustration of the chemical structure of a 3-cyanovinylcarbazole nucleoside (CNV-K) cross-linker used in some embodiments.

In some particular embodiments the cross-linker is 4-Thio-dT (FIG. 8A). Favre et al., J. Photochem Photobio B 32:109 (1998). In other embodiments, the cross-linker is 3-cyanovinylcarbazole nucleoside (CNV-K) (FIG. 8B). Yoshimura and Fujimoto Organic Lett. 10:3227 (2008). Although illustrated in FIGS. 9A and 9B with deoxyribose sugars, other sugars could be used instead, such as ribose, arabinose, or derivatives of similar sugars, as will be recognized by the skilled artisan. Both of these cross-linkers are photoactivatable cross-linkers and form cross-links between the probe and the target when the target is bound to the probe and the cross-linker is exposed to ultraviolet light.

In some embodiments, the cross-linkers can be positioned internal to the terminal nucleotides of the probe region. As discussed above, one or more cross-linkers can be positioned at least 1, 2, 3, 4, 5, 6, 7, 8, 9, 10 or more nucleotides in from a terminal nucleotide of the probe region of a cross-linking probe.

In some embodiments, one or more of the cross-linkers can be used in a single probe. Thus, in some embodiments, two or more cross-linkers, which can be the same type or different, can be employed in one probe. In some embodiments, 2, 3, 4, 5, 6, 7, 8, 9, 10, 11, 12, 13, 14, 15, 16, 17, 18, 19, 20 or more cross-linkers are used in one probe. In some embodiments, the cross-linkers are the same species. In some embodiments, two or more cross-linkers are different species, but have the same active group. In some embodiments, two or more different cross-linker types (e.g., Azo vs. benzophenones vs. furocoumarins) are used together on a single probe. In some embodiments, one or more photoactive cross-linkers are combined with one or more chemically activated cross-linkers. In some embodiments, one or more activatable cross-linker is combined with one or more conformationally activated cross-linker.

Functionalizing Oligonucleotide Probes with Cross-linkers

In some embodiments, oligonucleotide probes can be functionalized with cross-linkers in one or more of several ways. In some embodiments, the cross-linker(s) is/are incorporated at a position(s) internal to the probe rather than at the end. In some embodiments, functionalization can occur either before synthesis of the probe (e.g., the cross-linker-functionalized nucleoside(s) or nucleoside analog(s) is incorporated as a monomer(s)) or after synthesis. The cross-linkers can be chemically protected at one or more stages of probe synthesis and delivery to the target, for example during oligonucleotide synthesis if the cross-linker is incorporated as a monomer. In some embodiments, the protecting groups can be removed prior to probe delivery or afterward (in situ activation).

In some embodiments, cross-linkers can be attached to the backbone of a probe (the ribose sugar or phosphate for a natural DNA or RNA probe, or the corresponding chemical groups for a modified nucleic acid), for example by substitution of the 2'-hydroxyl group of ribose with a tethered cross-linker or by replacement of one of the phosphate oxygens with a tethered cross-linker.

In some embodiments, cross-linkers can be attached to one of the probe nucleobases (either a naturally-occurring base or a synthetic analog), for example by substitution of the C4 carbonyl oxygen with a thioether-linked cross-linker.

In some embodiments, cross-linkers can be incorporated in place of a nucleoside, replacing either the base or both the sugar and base with a cross-linking moiety.

In some embodiments, a cross-linker capable of forming covalent bonds with two nucleic acids (a bifunctional cross-linker, e.g. psoralen) can be allowed to form one of these bonds to the probe and the resulting monoadduct used to crosslink the target molecule. Alternatively, a monoadduct or chemically similar compound can be synthesized chemically and used as the cross-linker.

In some embodiments, multiple cross-linkers can be used in a single probe such that the overall yield of probes that form at least one covalent bond to the target is close to unity. In some embodiments, 1, 2, 3, 4, 5, 6, 7, 8, or more cross-linkers are used. The cross-linker(s) can be placed on either end or within the probe region. The placement of the cross-linkers within the probe region is especially advantageous. In some embodiments, where the probe region is comprised of two or more subparts, the cross-linker can be at a terminal end of one or more of the subparts.

In some embodiments, the cross-linking and cross-linker are non-promiscuous in that the cross-link is formed only between the probe region and its target and not simply to any molecule that is in the proximity of the bases that carry cross-linkers. In some embodiments, the efficiency is such that at least 80, 90, 95, 99, 99.5, 99.9, 99.99, 99.999, 99.9999, 99.99999% or more of the cross-linked probe is cross-linked to a sequence that hybridizes to the probe region upon activation of the cross-linker (if activation is required). For example, in some embodiments 10, 15, 20, 25, 30, 35, 40, 45, 50, 55, 60, 65, 70, 75, 80, 85, 90, 95, 96, 97, 98, 99, 99.9, 99.99, 99.999, 99.9999, 99.99999 or 100% of the cross-linking probe is cross-linked to a target nucleic acid that will hybridize to the probe region, including any range greater than any of the preceding values and any range defined between any two of the preceding values. In some in vitro applications, there need be no lower limit for the above noted percentages. On the other hand, in some embodiments, less than 10, 5, 1, 0.5, 0.1, 0.01, 0.001, 0.0001 or 0.00001% of the cross-linking probe in a sample is hybridized to a nucleic acid that is not a target nucleic acid.

In some embodiments, the cross-linker can be activated by the conformation change of the molecule. For example, in the probe region, bases carrying the cross-linker form Watson-Crick pairs between the probe region and the blocking region that are then replaced with wobble pairs to the mRNA target upon the binding of the probe region to the target. The cross-linkers have the property that they covalently link to their wobble-complement but not to their Watson-Crick complement (e.g., a G base carrying a cross-linker covalently binds to a U base but not to a C base). An example of such a cross-linker has been provided in (Coleman, R. S. and Pires, R. M. Covalent cross-linking of duplex DNA using 4-thio-2'-deoxyuridine as a readily modifiable platform for introduction of reactive functionality into oligonucleotides. Nucleic Acids Research, 1997. 25: p. 4771-4777; the entirety of which is incorporated herein by reference, including the disclosure regarding the cross-linker). In some embodiments, the cross-linker need not be activatable. Rather, the cross-linker can be one that would otherwise readily cross-link, if not for the presence of the blocking region. In such embodiments, one or more sections or subparts of the blocking region are selected so as to be inert to cross-linking (and thus avoiding the formation of initially cross-linked cross-linking probes) and the removal of the blocking region allows for the cross-linking of the cross-linker to the nucleic acid that displaces the blocking region. In some embodiments, these sections are made of orthogonal nucleotides or can simply be linkers or involve a backbone without the bases to which the cross-linkers cross-link to.

Imaging Applications

In some embodiments, the presence or absence of a detectable marker bound to a target through a probe can be detected by imaging a sample. In some embodiments, an actual image of the sample is not required and the sample can simply be reviewed for the presence or absence of any detectable marker.

Figure 2:
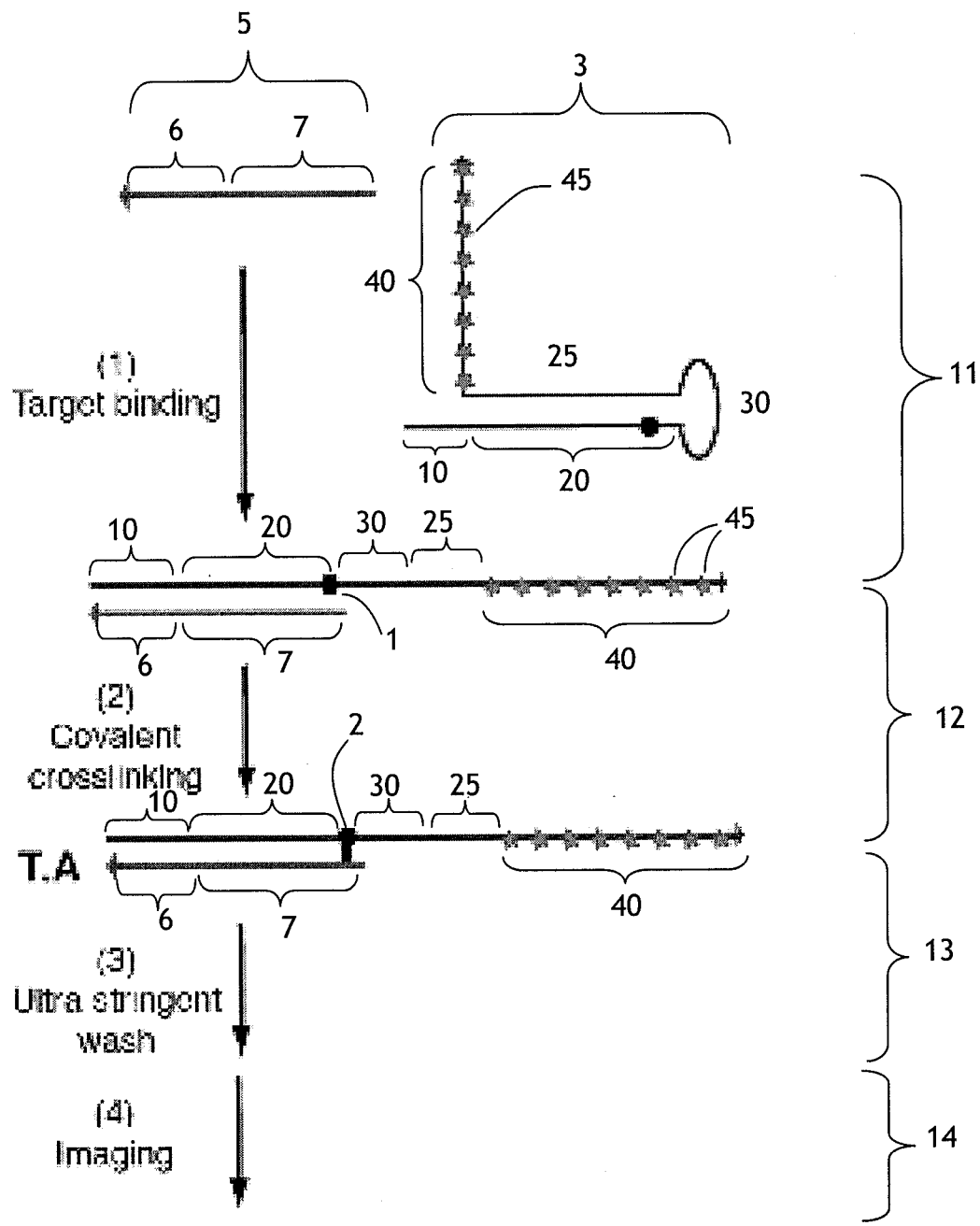
FIG. 2 depicts some embodiments of using a cross-linking probe.

In some embodiments, the detectable marker is selected from one or more of the following: fluorescent markers (including organic fluorophores, fluorescent nucleoside analogs, and inorganic semiconductor nanocrystals), chromogenic chemical substrates or enzymes, metallic particles, organic dyes, haptens for immunochemistry, commercially available fluorophores, including quantum dots. Of course, in some embodiments, the detectable marker need not emit radiation, for example, when surface plasmon resonance is used to detect binding, the detectable marker can be the probe region itself FIG. 2 depicts an embodiment of a cross-linking probe and a method of use in imaging applications. Initially, one binds the target nucleic acid, such as an mRNA, with a cross-linking probe(s) 3 (in process 11). The probe molecule 3 is introduced to the sample containing the target nucleic acid. The exposed initiator region 10 base-pairs to the target 5 at a first region 6, allowing rapid nucleation with the target (a kinetic effect) and providing affinity for the target via the formation of new base-pairs (a thermodynamic effect). After the probe 3 nucleates with the target mRNA via base-pairing at a first region 6, the target 5 base-pairs to the probe region 20 via a branch migration that opens a hairpin loop (which is an optional structure). The opening of the hairpin loop provides an entropic benefit that increases the strength of the interaction between the probe 3 and the target 5 (as would the dissociation of the blocking region if there is no loop). In some embodiments, the bases within the probe region carry activatable cross-linkers 1, which are now base-paired to the target 5. The blocking region 25 can provide a stringent specificity check that helps ensure that the bases carrying activatable cross-linkers 1 primarily (and, in some embodiments, only) pair to endogenous nucleic acids if they are specifically paired to the target 5. While not intending to be limited to theory, it is understood that this is because it is energetically unfavorable to open the stem to expose the cross-linkable bases 1 except via a branch migration process in which the intra-stem base pairs are replaced one-by-one by intermolecular base-pairs between the probe 3 and the target 5. The presence of each additional base pair in the stem between the initiator region 10 and the cross-linkable base(s) 1 increases the specificity stringency.

Next, one can covalently cross-link the probe region to the target in process 12. In some embodiments, one allows sufficient time for the probe molecules to diffuse into the sample and bind to target nucleic acids (e.g., mRNAs). Following this, the covalent cross-linkers 1 are activated, such as by photo-activation or as a result of change in conformation of the probe or environment, leading to probe-target covalent cross-linking, which includes at least one cross-link 2. In some embodiments, only those probes base-paired specifically to target nucleic acids are covalently linked to the sample. In some embodiments, all other probes become fused in the closed state due to covalent linking of the protection and propagation regions. As discussed herein, there are a variety of mechanisms for activating the cross-linking process, if one is employing an activatable cross-linker.

Once the specifically bound probes are covalently linked to the sample, it is possible to employ one or more ultra-stringent washes (process 13) that remove a significant amount of all other probes from the sample to yield exquisite specificity. In some embodiments, more of the other probes can be removed than would be typical from traditional washes, including washes that are not ultra-stringent. In some embodiments, all (or substantially all) of the non-cross-linked cross-linkable probes are removed. This can include any probes that are not hybridized to the sample, that are partially hybridized to the sample, or that are hybridized but not cross-linked to the sample. In some embodiments, essentially all probes that are not cross-linked to the target nucleic acid are removed. In some embodiments, substantially all of the uncrosslinked probe is removed. In some embodiments, substantially all of the detectable probe that has not been cross-linked to a non-probe nucleic acid is removed. In some embodiments, substantially all of the detectable probe that has not been cross-linked to a non-probe nucleic acid is removed. In some embodiments, the only unbound probe that remains after the wash is readily identifiable as being background. In some embodiments, 90% or more of the non-crosslinked probes are removed, for example 91, 92, 93, 94, 95, 96, 97, 98, 99, 99.9%, 99.99% or more of the uncrosslinked probe is removed. In some embodiments, the background signal per cell is less than the strength of the amplified signal for a correct target.

Once a significant amount of the non-crosslinked probe has been washed away, the sample can be imaged 14. In some embodiments, fluorescence microscopy can be employed to image the location of the cross-linked cross-linking probes, thus revealing the location of the target nucleic acids.

Figure 3:
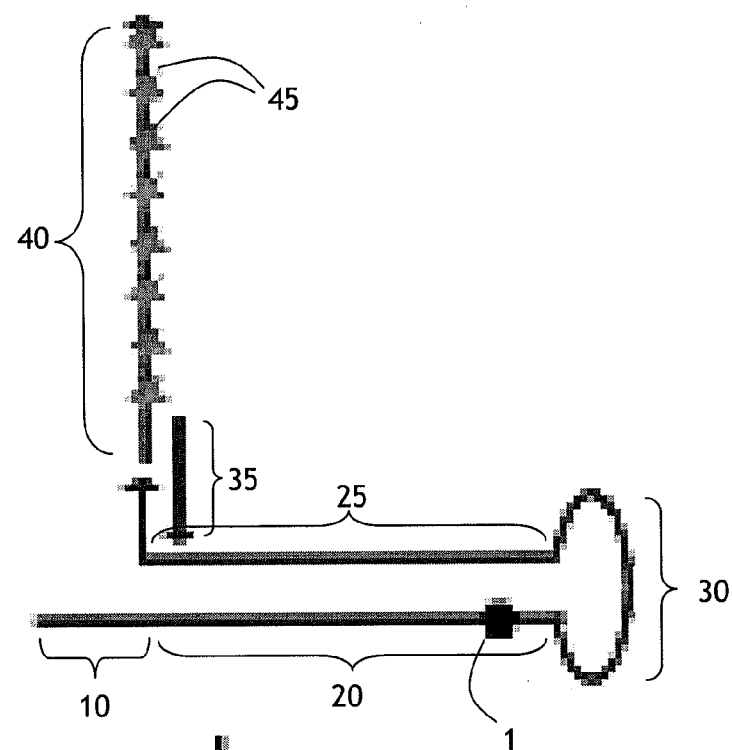
FIG. 3 depicts an embodiment of making a cross-linking probe.
Figure 3:
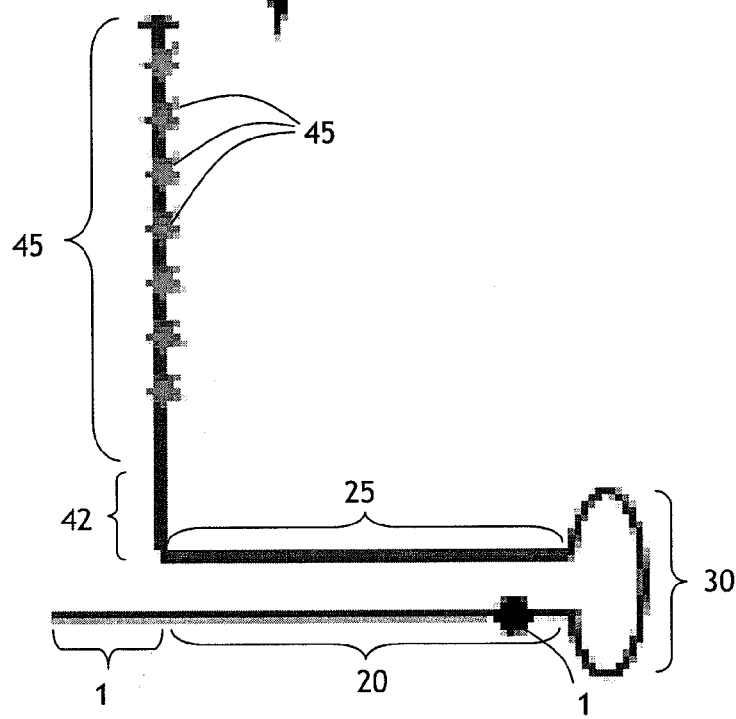

In some embodiments, the cross-linking probe, instead of carrying fluorophores on a single-stranded DNA tail, can employ branched DNA structures or other non-linear DNA structures as fluorophore carriers. In some embodiments, the detectable marker region 40 in the cross-linking probe 3 has an independent sequence from the probe region. Thus, the modular approach shown in FIG. 3 can be used for synthesizing some embodiments of the cross-linking probe. The detectable marker region 40 and the other part of the cross-linking probe (25, 30, 20, 10, and 1) are synthesized separately, and then ligated using nucleic acid 35 to link the two parts together to produce a complete cross-linking probe. In some embodiments, the detectable marker region 40 can have an independent sequence from the target, and thus, the detectable marker region can be reused for different targets.

Figure 4:
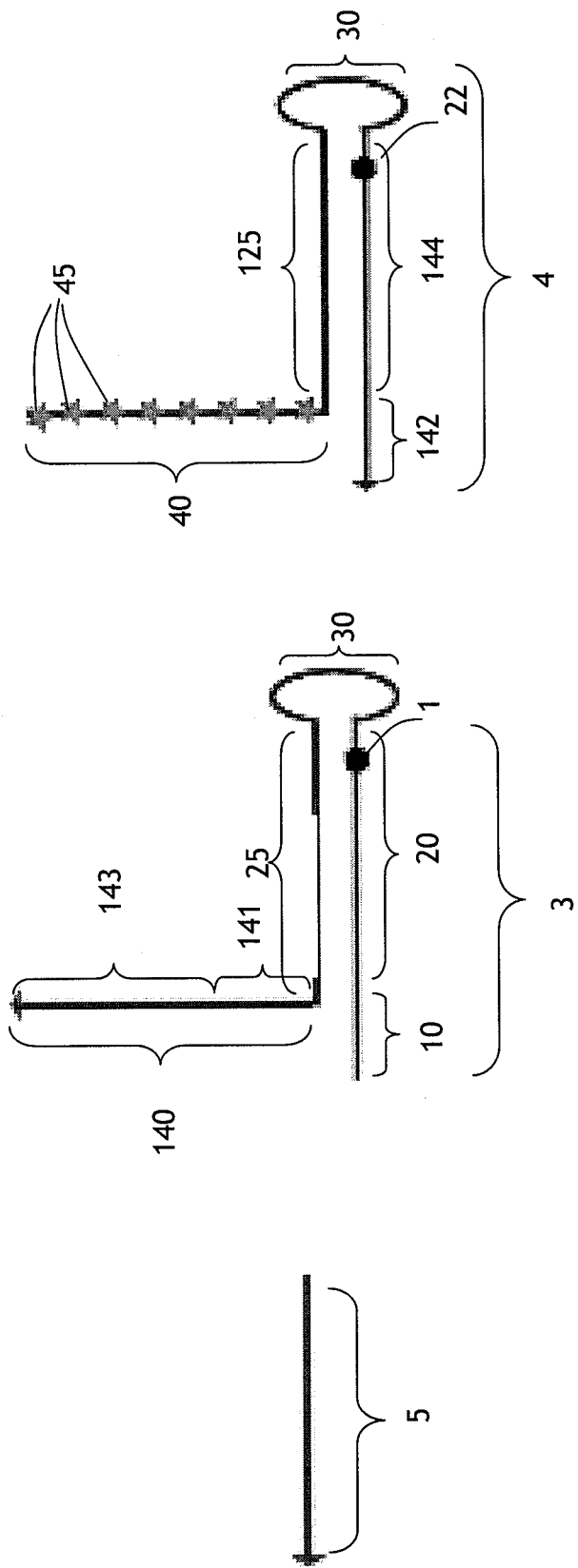
FIG. 4 depicts some embodiments of a cross-linking probe.

FIG. 4 depicts another embodiment of using a cross-linking probe. In this embodiment, while the probe 3, lacks a detectable marker region, the use of an amplifier molecule 4, allows for the addition of the detectable marker and/or region to be associated with the target, via the pairing region 140. In this embodiment, one allows the amplifier molecule 4 to bind to pairing region 140 via a complementary pairing region 142 and/or 144. In this embodiment, at least a part of the complementary pairing region 144 is blocked by a second blocking region 125. The amplifier molecule thus undergoes a conformational change, similar to that described for FIG. 2. One can then cross-link the amplifier molecule 4 to the cross-linked probe 3 via photo-activation of the cross-linker 22. Then one can perform an ultra-stringent wash to remove all other amplifiers from the sample. Thus, in some embodiments, multiple washes and multiple cross-linker activation steps can be performed. In some embodiments, multiple amplifier molecules can be used simultaneously such that each amplifier molecules targets the single-stranded tail of another species, with intermolecular covalent linkages formed only in the case of specific interactions. In some embodiments, those amplification polymers that are covalently linked to the target nucleic acid would be retained during the ultra-stringent wash.

Figure 5:
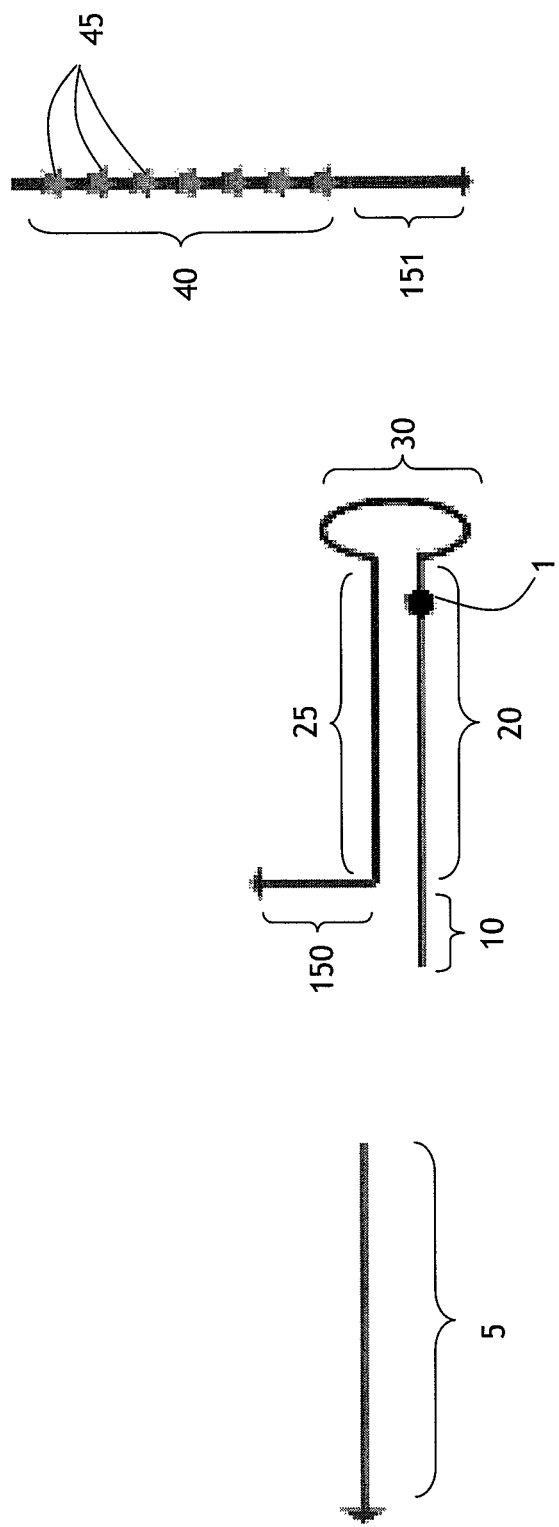
FIG. 5 depicts some embodiments of a cross-linking probe.

FIG. 5 depicts an embodiment which employs orthogonal base pairing (between pairing region 150 and a complementary pairing region 151) to replace the role of conformation change during amplification in the example above. In some embodiments, the pairing region 150 has no natural bases appearing consecutively in the pairing region of the amplifier strand 151 (for example natural bases could alternate with orthogonal bases such as iso-C and iso-G). In some embodiments, any orthogonal base combination that will avoid, prevent, or reduce hybridization of the pairing region to native or natural nucleic acids can be used. In some embodiments, the orthogonal bases can base-pair to each other (e.g. iso-C pairs strongly with iso-G) but cannot base-pair to the natural bases (see, e.g., Collins, M. L., et al., A branched DNA signal amplification assay for quantification of nucleic acid targets below 100 molecules/ml. Nucleic Acids Research, 1997. 25(15): p. 2979-2984). As a result, the amplifier molecules cannot significantly base-pair to endogenous nucleic acids because the natural bases in the amplifier strand would be able to form only isolated base-pairs separated by energetically unfavorable interior loops (i.e. few energetically stacked base pairs could result from these non-specific interactions). By placing orthogonal bases in the pairing region 150 (and/or complement 151), one can ensure that the complementary pairing region 151 (which will contain a sequence that can hybridize to the orthogonal bases and/or contain the orthogonal bases) will base-pair primarily (and in some embodiments only) to the molecule that includes the probe region. The same approach can be used for base-pairing of multiple amplifier molecules to form a linear or branched amplification polymer in which the complementary pairing region contains sufficient orthogonal nucleotides so as to prevent any substantial or effective base pairing between the complementary pairing region and other nucleotides in the sequences. In some embodiments, the complementary pairing region 151 contains no consecutive natural bases and intermolecular base-pairing between the amplification molecules is via a combination of natural and orthogonal base pairs.

Once one has an amplifier molecule with an orthogonal complementary pairing region 151 one allows the amplifier molecule 4 to bind to pairing region 150 via a combination of natural and orthogonal base pairs. One can then cross-link the amplifier molecule 4 to the molecule containing, linked to, or associated with the probe region 20. If the cross-linker 1, requires activation, then the activation step can also be performed. Following this, one can then use an ultra-stringent wash to remove effectively all other amplifier molecules 4 from the sample.

Figure 6:
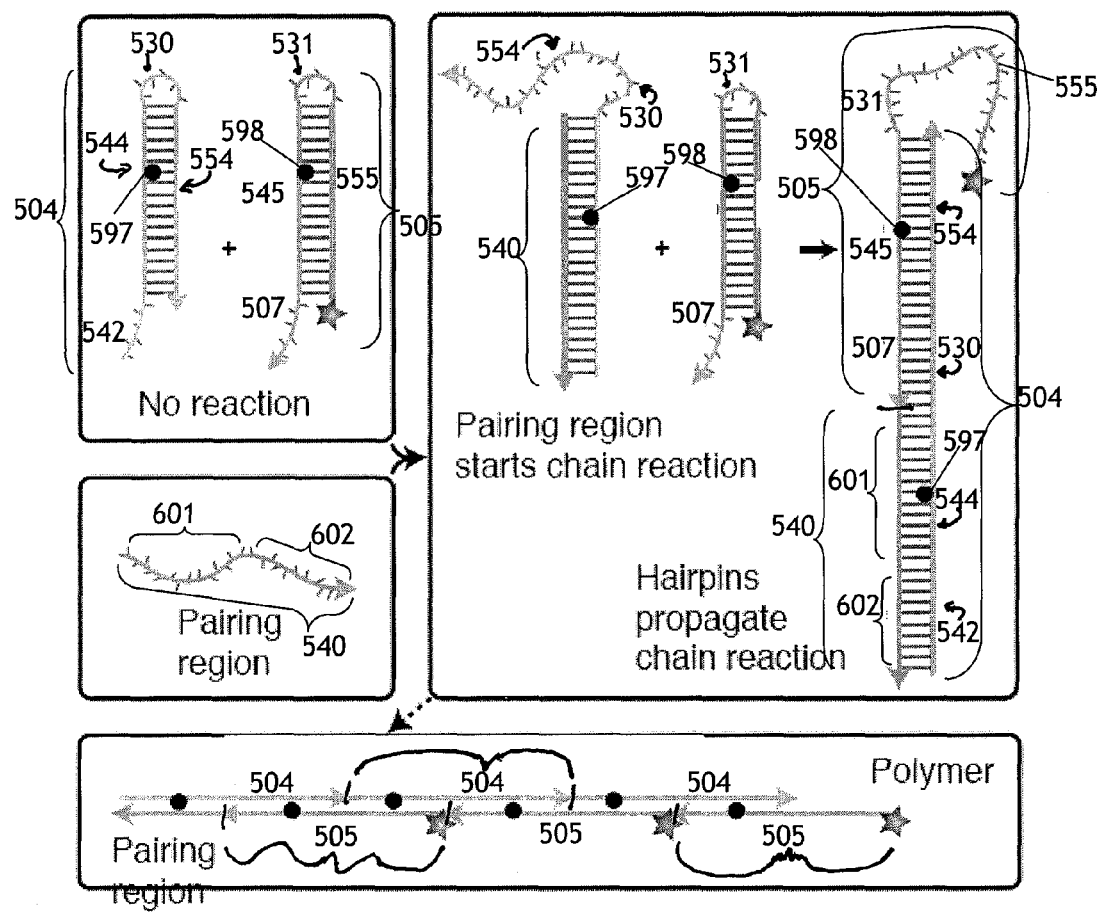
FIG. 6 depicts an embodiment of an HCR method employing a cross-linking probe.

FIG. 6 depicts another embodiment in which one can employ a cross-linking probe. As shown in FIG. 6, cross-linkers can be used in other blocked probe arrangements, such as in hybridization chain reactions, as discussed in U.S. Pat. Pub. Nos. 20060228733, 20050260635, and 20060234261, the entireties of each of which, including the discussion of hairpins and their use in hybridization chain reactions, and HCR itself are incorporated herein by reference. As can be seen in FIG. 6, in one embodiment, the pairing region 540 (with subregions 601 and 602) of a probe (only the pairing region is depicted in FIG. 6, the rest of the probe (which can be a shielded cross-linking probe) can be on either side of the pairing region) can be combined with two hairpins (504 and 505) that each include a crosslinker (597 and 598). The first hairpin 504 includes an initiator region 542 (complementary to 602), a complementary pairing region 544 (complementary to 601), a loop region 530, and a blocking region 554 that is complementary to 544. The second hairpin 505 includes a second initiator region 507 that is complementary to the loop region 530, another complementary pairing region 545 that is complementary to 554, a loop region 531, which is complementary to the initiator region 542, and a blocking region 555, that is complementary to region 545 and can be the same as region 554. As shown in the figure, these monomers can be allowed to form a polymer which will include the crosslinkers (598 and 597). In turn, the polymer can then be crosslinked, resulting in a crosslinked polymer. In some embodiments, the HCR scheme will also work when some or all the polarities of the strands are reversed (arrow at the opposite ends of the probe hairpin and the amplification hairpins). The stars in FIG. 6 represent optional detectable markers.

In some embodiments, any of the described embodiments herein will also work when some or all of the polarities are reversed.

In some embodiments, triggered covalent probes can be used to detect single nucleic acid target molecules as fluorescent puncta. For example, individual mRNA cross-linked to labeled probes can be identified as discrete puncta. Each puncta with a particular label has quantitatively similar intensity. In some embodiments, multiple probes are used to identify a variety of different targets. Probes for each target are labeled with a different colored fluorescent label and each puncta of a given color has a quantitatively similar intensity. Thus, the amount and location of the nucleic acid target(s) can be determined quantitatively. Using ultra-stringent washes allows the integral of the background signal for each cell to be small relative to the signal from a single puncta in the same cell.

In some embodiments, these properties are sufficient to ensure that the integrated total fluorescence provides quantitative readout of the target nucleic acid (e.g., mRNA) expression at lower magnification levels where the puncta cannot be distinguished. This property is useful for applications where the samples are too large to count puncta over the entire region of interest, or alternatively, for any application in which expression levels are high enough that puncta are not well separated.

In some embodiments, one can first dimension the structural components of the triggered covalent probes using in vitro assays and then proceed to in situ assays in fixed cells or tissues. In some embodiments, to maximize versatility and minimize cost, one can make the probes as short as possible subject to the constraint that the initiator region (toehold) is sufficiently long to facilitate rapid nucleation with the target and the stem is long enough to achieve stringent sequence filtering. Because branch migration is used to ensure specificity prior to cross-linking, increasing the length of the toehold does not ultimately represent a tradeoff between affinity and specificity as it would for a traditional single-stranded probe.

In some embodiments, if desired, the target nucleic acids (e.g., mRNAs) can be targeted by multiple probes that bind contiguously along the single target (e.g., mRNA) to increase the strength of the cognate signal. This may also cooperatively defeat native mRNA secondary structure.

In some embodiments, following cross-linking, ultra-stringent washes can be used to destabilize all base pairs in the sample (specific and non-specific). Commercially available In some embodiments, one or more of the herein disclosed embodiments are employed on a "DNA chip"-type application. For example, in some embodiments the probe region (which is shielded as described herein) is attached to the chip and the target is crosslinked to the chip, via the probe region only if it displaces the blocking region (which could then be washed away from the chip). In some embodiments, the probe region can be immobilized on any solid surface and then employed to pull out or detect the target nucleic acid.

Existing in situ hybridization bioimaging methods share the weakness that the background signal is raised by amplification of probes that bind non-specifically within the sample (Qian, X., L. Jin, and R. V. Lloyd, In situ hybridization: basic approaches and recent development. The Journal of Histotechnology, 2004. 27(1): p. 53-67). In some embodiments, the shielded cross-linking methods or probes can be employed to avoid or reduce this issue. One of skill in the art will also appreciate that in other embodiments, the cross-linking probes or methods do not avoid or reduce this issue.

In some embodiments, the use of the present cross-linking probes allows the detailed analysis of genetic regulatory processes.

In some embodiments, the probe and/or technique is specific, in that fluorescence signals are generated at the site of a target molecule (and in some embodiments can minimize or reduce false positives).

In some embodiments, the probe and/or technique is sensitive, in that the fluorescence signal is strong enough to enable imaging of single target molecules (and in some embodiments can minimize false negatives).

In some embodiments, the probe and/or technique is multiplexed, in that the amplification of all probe species can be performed simultaneously in parallel (and in some embodiments can enhance efficiency and reduce sample degradation).

In some embodiments, the probe and/or technique is quantitative, in that it allows quantized fluorescent signaling per target molecule (and in some embodiments can allow for relative quantification of target abundance within samples).

In some embodiments, regardless of the nature of any subsequent downstream amplification step, the present probe concept is superior to other existing probe strategies with regard to conferring specificity.

In embodiments in which the probes carry sufficiently many fluorophores of sufficient brightness and the detection device is sufficiently sensitive, then no further amplification is necessary. In some embodiments, additional amplification is desirable to increase the signal strength associated with each target molecule. In performing this amplification, it is valuable to retain the specificity that was achieved during the detection stage.

In some embodiments, the above detection and amplification schemes can be used to target multiple nucleic acid targets simultaneously by using probe and amplifier sequences that are orthogonal in sequence space. Thus, multiplexing becomes possible.

In some embodiments, the detection and amplification schemes disclosed herein can be used to produce quantized fluorescent signal strength associated with each target nucleic acid that has been covalently linked to a probe molecule (and optionally to a number of additional fluorescently-labeled amplifier molecules).

In some embodiments one can employ a cross-linking probe in situations where the size of the fluorophore-carrying segment hinders penetration into the sample. In such embodiments, nucleated dendrimers (as described in P. Yin, H. M. T. Choi, C. R. Calvert, N. A. Pierce. Programming biomolecular self-assembly pathways. Nature, 451:318-322, 2008; U.S. Pat. Pub. Nos. 20090011956; and 20060234261, the entireties of each of which, including the various teachings regarding dendritic growth and HCR, are incorporated herein by reference) can be used to deliver one or more fluorophores bound to the binding probe (or a molecule associated therewith). In some embodiments, orthogonal isoC/isoG bases can be interspersed with natural bases to ensure that the dendrimer components do not base-pair non-specifically with native nucleic acids. After (or with) the assembly of the amplification dendrimer attached to the target nucleic acid/binding probe complex, the dendrimer can be covalently cross-linked to the binding probe (or molecules associated or linked thereto), and each branch of the dendrimer can be covalently linked to its parent branch. In such embodiments, the initial components of the branches can all (or some fraction thereof) include a cross-linker which can (but need not be) activatable. In some embodiments, a subsequent stringent wash can be applied to remove all other non-specifically-bound amplification molecules. In some embodiments, cross-linkers can be used in other blocked probe arrangements, such as in hairpins in hybridization chain reactions, as discussed in U.S. Pat. Pub. Nos. 20060228733 and 20060234261, the entireties of both of which, including the discussion of hairpins and their use in hybridization chain reactions, are incorporated herein by reference.

Disruption of Nucleic Acid Function, Gene Silencing and Therapeutic Applications In some embodiments, cross-linking probes can interact with and covalently bind target nucleic acid sequences to interfere with or prevent the normal function of the target. This can be carried out in vitro or in vivo. In some embodiments, the target nucleic acid sequence is an mRNA sequence and covalent binding of the probe to the target inhibits splicing or translation of the target mRNA, thereby reducing or silencing expression from a target gene. In other embodiments the target is a tRNA, miRNA, rRNA or piRNA and covalent binding of the probe to the target disrupts the role of the target by preventing the nucleic acid from carrying out its normal function. In other embodiments the target is a DNA molecule and covalent binding of the probe to the target disrupts the role of the target by preventing the DNA from carrying out its normal function.

A disease or disorder can be treated and/or prevented by targeting diseased cells or pathogenic organisms and silencing or reducing the expression of selected genes in the cells or organisms. In some embodiments, reducing gene expression or gene silencing can be used to treat a disease or disorder by reducing expression of a gene whose expression is associated with the disease or disorder. In other embodiments genes necessary for the survival of diseased cells can be silenced, leading to the death of the diseased cells, such as tumor cells. In other embodiments, reduced expression or silencing of a gene necessary for infection by a pathogenic organism can be used to treat or prevent infection by the organism. In some embodiments, more than one gene can be targeted in a single cell or organism using multiple cross-linking probes. For example, two, three or more nucleic acid targets (e.g., DNA, RNA, tRNA, rRNA, mRNA, miRNA, piRNA, other small RNAs) may be targeted using multiple different cross-linking probes.

In other embodiments, regulatory nucleic acids including (but not limited to) miRNAs and siRNAs are targeted. Cross-linking of these nucleic acids by the probe inhibits these nucleic acids from performing their normal roles. In some embodiments, targeting regulatory nucleic acids may reduce or enhance expression of genes not directly targeted by the probe.

In other embodiments, nucleic acids can be targeted that are present in cells related to a disease or disorder such as tumor cells, or HIV-infected cells, or bacteria that infect a host, or auto-reactive T-cells that cause an auto-immune disease.

Nucleic acid strands (e.g., mRNA) can be targeted such that cross-linking probes will only cross link in the presence of the target nucleic acid containing the targeted sequence. If a nucleic acid subsequence is chosen that is only expressed in certain types of cells e.g. cells with a particular genetic mutation or signature sequence, then covalent cross-linking will only occur in the targeted cells. Cross-linking of cross-linking probe to nucleic acids will not occur in cells without the target.

In some embodiments, introduction of a cross-linking probe leads to the covalent cross-linking of the probe region of the probe to a target nucleic acid (e.g., DNA, RNA, mRNA, miRNA, piRNA, tRNA, rRNA, and other small RNAs). This leads to gene silencing of the target in cells comprising the disease-associated target (such as diseased cells or pathogenic organisms).

In some embodiments, if desired, the targets (e.g., mRNAs) can be targeted by multiple probes that bind at different locations (e.g., contiguously) along single target molecules (e.g., mRNA) to increase the inhibition of expression.

The design of the cross-linking probes can be adjusted such that they bind specifically to the desired nucleic acid targets. The design can be derived from sequences derived from literature reviews and disclosed in, for example, various databases (e.g. NCBI).

In some embodiments, the target can be a sequence of at least a portion of a gene. In some embodiments, the gene can be a housekeeping gene. Housekeeping genes are known in the art, and a list of housekeeping genes is provided in, for example, Eisenberg et al., *Trends in Genetics,* 2003, 19(7): 362-365, which is hereby incorporated by reference in its entirety. In some embodiments, the gene can encode a structural protein such as, for example, actin or tubulin. In some embodiments, the target sequence can be an mRNA encoding a motor protein, such as, for example, kinesin. In some embodiments, the gene can encode an enzyme involved in cell metabolism such as, for example, glyceraldehyde-3-phosphate dehydrogenase, phosphoglycerate kinase, dehydrogenase ATP synthase, glycogen synthase kinase 3 alpha, and the like. In some embodiments, the gene can encode a ribosomal protein. In some embodiments, the gene can encode a cell cycle regulatory molecule such as, for example, p21, p19ARF, or cyclin. In some embodiments, the gene can encode an enzyme involved in protein degradation such as, for example, a ubiquitin activating enzyme or a ubiquitin-conjugating enzyme. In some embodiments, the gene can encode a kinase, such as, for example, protein kinase C. In some embodiments, the target can be a cell death regulatory molecule such as, for example, apoptosis inhibitor 5 (APIS) or a Bcl-2 family member. In some embodiments, the gene can encode a transcription factor. In some embodiments, the gene can encode a polymerase, such as RNA polymerase I. In some embodiments, the gene can encode an oncogene, such as c-myc, src or c-ras. In some embodiments, the gene can encode PKR. In some embodiments, the gene can encode an inhibitor of PKR. In some embodiments, the gene can incode a virus (e.g., HIV). In some embodiments, the gene can be present in one or more bacteria but not in eukaryotic cells.

In some embodiments, the target can be a sequence that is necessary for the life cycle or replication of a pathogenic organism, such as a virus or bacteria.

In some embodiments, a disease to be treated is to be treated by down-regulation of expression and the nucleic acid target is typically one that is not expressed in healthy cells or at least to a lesser extent in healthy cells. In some cases, a disease may be treated by targeting several nucleic acid targets with different probes.

Diseases contemplated for treatment in embodiments of the invention include any disease in which a genetic target can be bound to a cross-linking probe. Such embodiments include treatment of diseases such as, for example, cancer, AIDS, and infectious diseases, such as bacterial infection. Infectious diseases refer to any disease caused by pathogens, including, for example, viruses, bacteria, fungi and protozoa. In some embodiments, the nucleic acid molecule is a nucleic acid molecule associated with a disease or disorder, such as a mutant nucleic acid molecule (e.g., a cancer mutation). In some embodiments, the nucleic acid molecule is associated with an auto-immune response (e.g., a nucleic acid molecule encoding all or part of an auto-reactive T-cell receptor)

In some embodiments, the disease to be treated is a type of cancer, such as, for example, leukemia, carcinoma, lymphoma, astrocytoma, sarcoma including Ewing's sarcoma, glioma, glioblastoma, retinoblastoma, melanoma, Wilm's tumor, bladder cancer, breast cancer, colon cancer, hepatocellular cancer, pancreatic cancer, prostate cancer, lung cancer, liver cancer, stomach cancer, cervical cancer, testicular cancer, renal cell cancer, and brain cancer.

In other embodiments, the disease to be treated is associated with infection by an intracellular parasite. For example, the intracellular parasite may be a virus such as, for example, an adenovirus, cytomegalovirus, Epstein-Barr virus, herpes simplex virus, human herpesvirus 6, varicella-zoster virus, hepatitis viruses, papilloma virus, parvovirus, polyomavirus, measles virus, rubella virus, human immunodeficiency virus (HIV), or human T cell leukemia virus. In other embodiments, the intracellular parasite may be a bacterium, protozoan, fungus, or a prion. More particularly, the intracellular parasite can be, for example, Chlamydia, *Listeria, Salmo-* nella, Legionella, Brucella, Coxiella, Rickettsia, Mycobacterium, Leishmania, Trypanasoma, Toxoplasma, and Plasmodium.

In some embodiments, the target can be a sequence that is necessary for the life cycle or replication of a virus or other pathogenic organism, such as, for example, gene expression of the virus and the expression of a cellular receptor or co-receptor necessary for viral replication. In some particular embodiment of the invention, the virus is the human immunodeficiency virus (HIV). The target sequence may be, for example, selected from the group consisting of Rev, Gag, Pol, LTRs, TAR, RRE, Ψ, att, pbs, ppt and other essential DNA and RNA cis-regulatory elements. In one embodiment of the invention, the target is an expressed region of the HIV viral genome, for example, a portion of the 9-kb transcript of the integrated HIV virus, or any of the variously spliced mRNA transcripts of HIV (Schwartz, S; Felber, B K; Benko, D M; Fenya, E M; Pavlakis, G N. Cloning and functional analysis of multiply spliced mRNA species of human immunodeficiency virus type 1. *J. Virol.* 1990; 64(6): 2519-29). Target regions within the HIV transcripts can be chosen to correspond to any of the viral genes, including, for example, HIV-1 LTR, vif, nef, and rev.

In some embodiments, the target can be a sequence that is necessary for the life cycle or replication of a tumor cell. In other embodiments, the detection target can be a sequence that is indicative of a pre-cancerous state, such as, for example, an oncogene sequence.

Embodiments of the subject matter include compositions for treating a disease. The compositions can include a cross-linking probe comprising a probe region sequence that can bind to a desired nucleic acid target and one or more cross-linkers that can be activated to cross-link the probe to the target upon binding of the probe region to the target. When the cellular target is an mRNA, the probe region sequence will generally comprise a nucleic acid sequence complementary to at least a region of the target mRNA.

The compositions can be formulated with a variety of carriers to facilitate introduction into a cell. Suitable carriers can include, for example, polymers, proteins, carbohydrates and lipids. For example, a cyclodextrin-containing polymer can be used for the delivery of the cross-linking probes. Delivery of nucleic acids can be accomplished as described by Heidel (Heidel, J. D. 2005. Targeted, systematic non-viral delivery of small interfering RNA in vivo. Doctoral thesis, California Institute of Technology. 128p., herein incorporated by reference in its entirety). Also contemplated within the scope of the subject matter are gene delivery systems as described by Felgner et al. (Felgner et al. 1997. *Hum Gene Ther* 8:511-512, herein incorporated by reference in its entirety), including cationic lipid-based delivery systems (lipoplex), polycation-based delivery systems (polyplex) and a combination thereof (lipopolyplex). Cationic lipids are described in U.S. Pat. Nos. 4,897,355 and 5,459,127, each of the foregoing which is herein incorporated by reference in its entirety. Proteins can also be used for cross-linking probe delivery, such as synthetic neoglycoproteins (Ferkol et al. 1993. *FASEB J* 7:1081-1091; Perales et al. 1994. *Proc Nat Acad Sci* 91:4086-4090; each of the foregoing which is herein incorporated by reference in its entirety). epidermal growth factor (EGF) (Myers, EPO 0273085, herein incorporated by reference in its entirety), and other ligands for receptor-mediated gene transfer (Wu and Wu. 1987. *J Biol Chem* 262(10): 4429-4432; Wagner et al. 1990. *Proc Natl Acad Sci USA* 87(9):3410-3414; Ferkol et al. 1993. *J. Clin Invest* 92(5): 2394-2300; Perales et al. 1994. *Proc Natl Acad Sci USA* 91(9):4086-4090; Myers, EPO 0273085; each of the foregoing which is herein incorporated by reference in its entirety). Viral and viral vector-like delivery systems generally known in the art, such as those described in U.S. Pat. Nos. 7,0333,834; 6,899,871; 6,555,367; 6,485,965; 5,928,913; U.S. patent application Ser. Nos. 10/801,648; 10/319,074, and 09/839,698, each of the foregoing which is herein incorporated by reference, are also contemplated for use in the present subject matter. In addition, standard electroporation techniques can be readily adopted to deliver probes to cells.

In some embodiments, cross-linking probes can be delivered to cells in vivo such as by, for example, injection of the probes within a delivery vehicle into the bloodstream or by intramuscular, subcutaneous, or intraperitoneal means. An appropriate means of delivering cross-linking probes to a desired population of cells can be identified by the skilled practitioner based on the particular circumstances without undue experimentation. Following delivery, and at a desired time, such as after a sufficient amount of time to allow probes to interact with target, the probes can be cross-linked to the target nucleic acids. As discussed above, in some embodiments activation is via the provision of an external stimulus, such as light. The external stimulus can be provided to a limited spatial area in order to limit cross-linking to that area. In other embodiments, probes comprise cross-linkers that are able to cross-link the blocking region is removed by binding to the target and cross-linking occurs upon hybridization.

Some embodiments involve methods of treating a patient suffering from a disease or disorder such as, for example, a bacterial infection. In some embodiments the methods comprise administering to target cells in the patient, such as the bacterial cells, an effective amount of cross-linking probe having a probe region that is preferably at least 80%, more preferably at least 90%, 95%, 96%, 97%, 98%, 99% or higher complementary to a portion of a target nucleic acid, such as a nucleic that is necessary for the survival or infectious nature of the bacteria. Preferably, the probe region is substantially complementary to at least a portion of the target nucleic acid. In some embodiments, the probe region can be completely complementary to a nucleic acid that is associated with the disease. For example, the cross-linking may be designed such that the probe region covalently binds to an oncogenic mRNA or a bacterial gene transcript.

Following administration, the cross-linker may be activated, if necessary, such as by provision of an external activating agent. In some embodiments, a particular area of the patient, in which target associated with the disease or disorder is located, is exposed to the activator. For example, the area of the bacterial infection may be exposed to an activator such as light to cause the probe that is bound to target nucleic acids to cross-link.

Compositions and Kits for Covalent Cross-linking and Therapeutic Benefit

Compositions and kits for covalently bonding a probe to a target nucleic acid are contemplated for use within the scope of the subject matter. In some embodiments, the compositions comprise a cross-linking monomer as described herein. Upon delivery to a target cell, tissue or sample and recognition of the target, the cross-linker is activated and the probe region of the probe is cross-linked to the target.

The compositions can also contain other components, such as, for example, accessory molecules that facilitate target binding or, in some embodiments, detection of the target-bound probe.

Furthermore, the composition can comprise a carrier that facilitates the introduction of the cross-linking probe into a cell, tissue or other sample containing a target nucleic acid, such as a cell or organism comprising a target gene associated with a disease or disorder. Carriers for delivery of nucleic acids into cells are well known in the art and some are described above.

A kit for gene silencing or target detection typically comprises the compositions as described in detail above. In embodiments in which an external activator is used to trigger cross-linking, the kits may also comprise such an activator. The activator will be appropriate for the cross-linker that is present in the probe. In some embodiments the activator may be, for example, a light probe for supplying light of a wavelength that will activate a photo-activatable cross-linker.

In some embodiments, kits are provided for gene silencing and can be used to deliver cross-linking probe to a population of cells comprising a disease-associated gene target as well as to healthy, wild-type cells. In other embodiments, the kit can be used to identify a detection target in vitro or in situ. Again, the kits may further comprise an activator for cross-linking the cross-linking probes to the targets.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1

Nucleic Acid Cross-linking

This example illustrates the use of a cross-linking probe to attach a cross-linker to target nucleic acid, such as an mRNA.

One first obtains a cross-linking probe that includes an initiator region, a probe region that hybridizes to the desired target nucleic acid, a blocking region that obstructs the cross-linker when bound to the probe region, and a light activatable cross-linker. One then adds the cross-linking probe to the cell or tissue that is believed to include the target nucleic acid and allow the cross-linking probe to hybridize to the target. One then activates the cross-linker by irradiating the cell or tissue. Following this, the cross-linker will cross-link to the target nucleic acid, resulting in a cross-linked target.

Example 2

In Situ Hybridization

This example illustrates a use of a cross-linker probe in an in situ hybridization. One performs the steps outlined in Example 1, except that the cross-linking probe also initially includes a detectable marker region (with one or more detectable markers) that is attached to the blocking region.

Following irradiation, one then washes the tissue or cell using an ultrastringent wash containing denaturing chemicals such as formamide and/or performing the wash at elevated temperatures. Following this, one then images the remaining detectable markers in the cell or tissue in order to identify whether or not, where, and how much of the target nucleic acid is present.

Example 3 mRNA In Situ Hybridization Using a Hairpin Amplifier Molecule

This example illustrates a use of a cross-linker probe in an in situ hybridization. One performs the steps outlined in Example 2, except that the cross-linking probe also initially includes a pairing region that is attached to the blocking region.

Following the irradiation, one then washes the tissue or cell via an ultrastringent wash protocol to remove a significant portion of the unbound cross-linking probe. Following this, one then adds the amplifier molecule, which includes a detectable marker region (with decteable markers) and a complementary pairing region that will bind to the pairing region on the cross-linking probe. The amplifer molecule can have the general structure depicted in FIG. 4, and the amplifier molecule can include at least one photoactivatable cross-linker in the complementary pairing region. Following this, one can then irradiate the cell or tissue a second time to cross-link the cross-linker in the amplifier molecule. Following the second irradiation, one then washes the tissue or cell to remove a significant portion of the unbound amplifier molecule.

Following this, one then images the remaining detectable markers in the cell or tissue in order to identify whether or not, where, and how much of the target nucleic acid is present.

Example 4

Nucleic Acid Hybridization Using a Orthogonal Base Containing Amplifier Molecule This example illustrates a use of a cross-linker probe in an in situ hybridization. One performs the steps outlined in Example 2, except that the cross-linking probe also initially includes a pairing region that is attached to the blocking region.

Following the irradiation, one then washes the tissue or cell via an ultrastringent wash protocol to remove a significant portion of the unbound cross-linking probe. Following this, one then adds the amplifier molecule, which includes a detectable marker region (with detectable markers) and a complementary pairing region that will bind to the pairing region on the cross-linking probe and that has no consecutive natural nucleotides. The amplifer molecule can be that depicted in FIG. 5, and the amplifier molecule will include a complementary pairing region that can bind to the pairing region in the cross-linking probe. Following this, one then washes the tissue or cell to remove a significant portion of the unbound amplifier molecule.

Following this, one then images the remaining detectable markers in the cell or tissue in order to identify whether or not, where, and how much of the target nucleic acid is present.

Example 5

Tethered psoralens were prepared via two commercially-available products: a trimethylpsoralen (TMP) phosphoramidite 1007 (see, e.g., FIG. 7) for incorporation at the 5'-terminus of an oligonucleotide during solid-phase synthesis and a succinimidyl ester derivative 1008 (see FIG. 7) of psoralen that can be conjugated to an amine-modified oligonucleotide post-synthetically.

Figure 7:
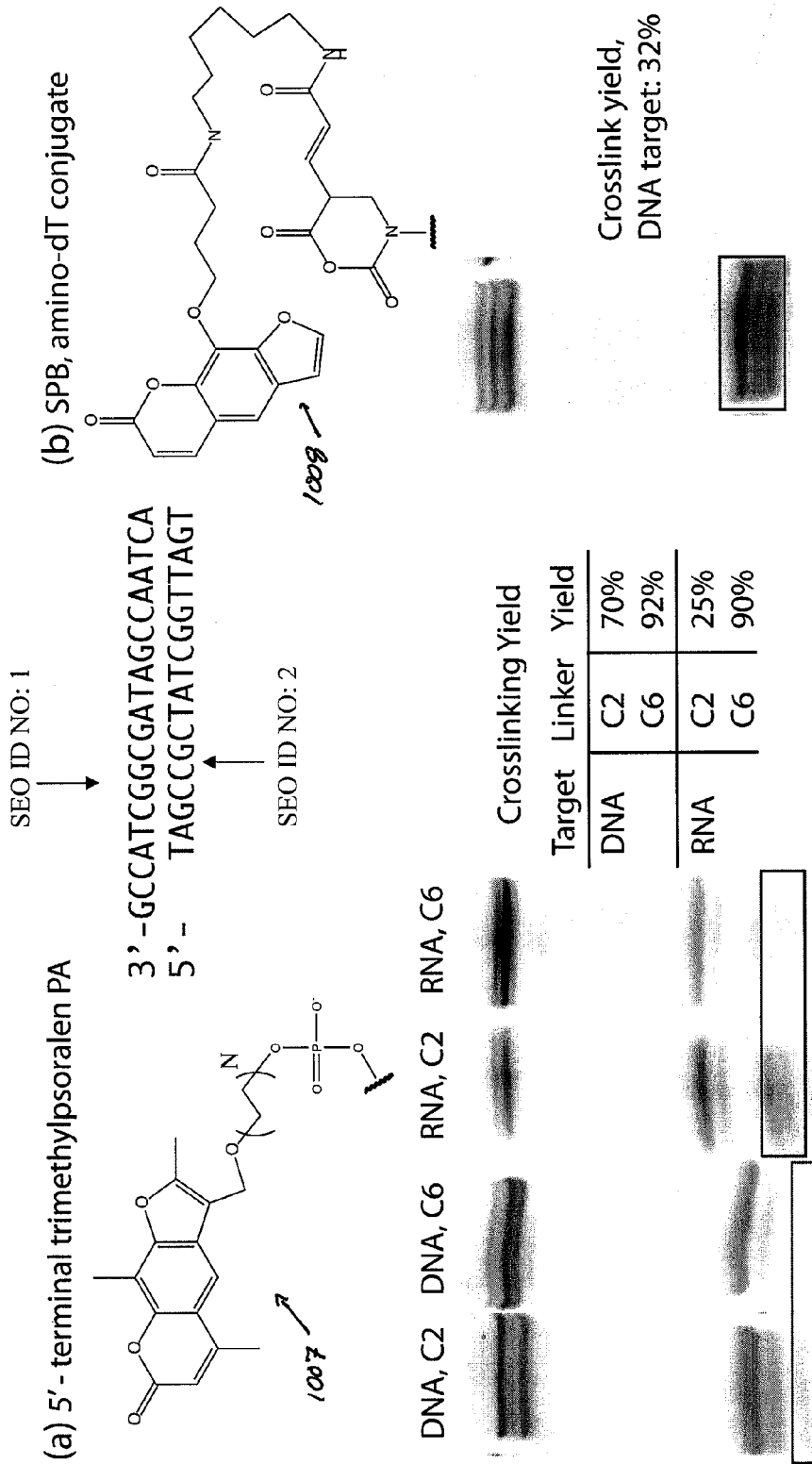
FIG. 7 depicts two different photoactivatable crosslinkers and the gel results from Example 5.

18 mer probes were either: (a) synthesized using 5'-terminal trimethylpsoralen phosphoramidite (Glen Research), or (b) labeled post-synthetically by conjugation of succinimidyl ester of 8-yloxy psoralen 8 (SPB, Pierce) to amine modified thymine. Probes were hybridized to 21 mer targets and irradiated with 365 nm UV light for 30 min (30 mW/cm2, TMP saturated after 5 minutes, SPB 25 minutes), then analyzed by denaturing gel electrophoresis. The gels were post-stained with SyBr Gold (Invitrogen) and crosslinking yield determined by comparing the intensity of non-crosslinked target band (red box) to non-irradiated controls. The results are shown in FIG. 7.

The efficacy of both molecules in cross-linking DNA and RNA targets in vitro were examined. When attached to a probe by a 2-carbon linker, TMP cross-linked duplex DNA with moderate efficiency, but was much less effective at cross-linking to an RNA target. The results for both of these molecules are shown in FIG. 7. The 6-carbon linker enabled TMP to efficiently bind both DNA and RNA targets. The succinimidyl derivative of psoralen can be added to an oligonucleotide at any position, but the cross-linking yields are lower than for the terminal TMP.

Example 6

Figure 9:
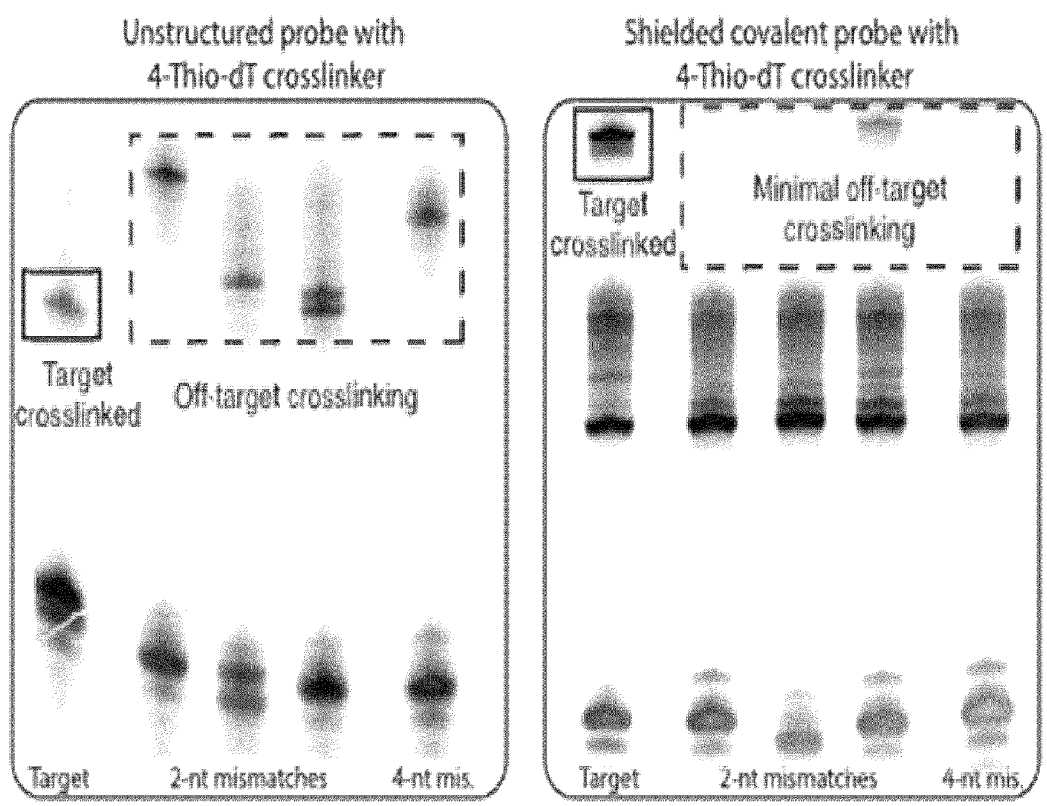
FIG. 9 shows the improved selectivity of shielded probes compared to traditional unstructured probes using 4-Thio-dT as a cross-linker.

A shielded cross-linking probe was constructed comprising an initiator region and a probe region that were complementary to a 23-nt target oligonucleotide (deoxy-[5'-CATGT-CAACCGTTCCTGCGAGTA-3']) (SEQ ID NO:3). The probe contained a 5-nt single-stranded initiator region and an 18-base pair duplex closed by a 6-nt hairpin loop (shown schematically in FIG. 1A), A single 4-Thio-dT cross-linker (FIG. 9) was positioned in the probe region 4 nt from the loop end such that it would be hybridized to the fourth nucleotide (dA) from the 3' end of the target once probe-target hybridization and branch migration were complete. A blocking region formed a duplex with the probe region and thus shielded the crosslinkers. A 23-nt single-stranded (unstructured) probe was also constructed containing the same probe sequence without the blocking region and hairpin loop. Separately, the shielded and unstructured probes were hybridized (30 minutes at RT in 1×SSC buffer—150 mM sodium chloride, 15 mM sodium citrate, pH 7.2) with the target sequence as well as with several decoy targets. The decoy targets consisted of 23-nt oligonucleotides (sequences: deoxy-5'-CAT-GTCAACCGTTCCTGGAAGTA-3' (SEQ ID NO:4), deoxy-5'-CATGTCAACCGAGCCTGCGAGTA-3' (SEQ ID NO:5), deoxy-5'-CATGTATACCGTTCCTGCGAGTA-3' (SEQ ID NO:6), deoxy-5'-CATGTCAACCGAGGATGC-GAGTA-3' (SEQ ID NO:7)) differing from the correct target by either 2 or 4 nucleotides, as indicated in FIG. 9. After hybridization, the reactions were irradiated with 365-nm ultraviolet light for 18 minutes at 4 degrees C. Aliquots were then removed from the reactions and analyzed by denaturing electrophoresis on 15% polyacrylamide gels according to standard techniques. The gels were visualized by post-staining with SyBr Gold™ nucleic acid stain and imaged using a fluorescent gel scanner.

As can be seen in FIG. 9, the shielded cross-linking probes containing the 4-Thio-dT cross-linkers showed improved selectivity compared to the traditional unstructured probes. Unstructured probes cross-linked both the correct target sequence, as well as decoy sequences containing 2 or 4 mismatched nucleotides. In contrast, the shielded covalent probe discriminates against 2 of the 32-nucleotide mismatches and also discriminates against the 4-nucleotide mismatch.

Example 7

A shielded cross-linking probe was constructed comprising an initiator region and a probe region that were complementary to the same target nucleic acid sequence described in Example 6. The probe comprised a hairpin with the same sequence and dimensions as in Example 6, except that the 4-Thio-dT crosslinker was replaced with dT and a single 3-cyanovinylcarbazole (CNV-K) crosslinker (FIG. 8B) was positioned such that it would be hybridized to the $9^{th}$ nucleotide (dC) from the 3'-end of the target sequence once probe-target hybridization and branch migration was complete. This position was chosen such that the CNV-K cross-linker would form a cross-link with the adjacent dT upon ultraviolet irradiation. A blocking region formed a duplex with the probe region and thus shielded the cross-linkers. As in Example 6, an unstructured probe was also constructed with the same sequence and crosslinker but lacking the blocking region and hairpin loop. The probes were hybridized to the same correct and decoy (mismatched) targets and irradiated as in Example 6, except that the duration of irradiation was shortened to 5 minutes due to the greater sensitivity of the CNV-K crosslinker. The reactions were analyzed in the same way as described for Example 6, and an image of the resulting gel lanes is shown in FIG. 10.

Figure 10:
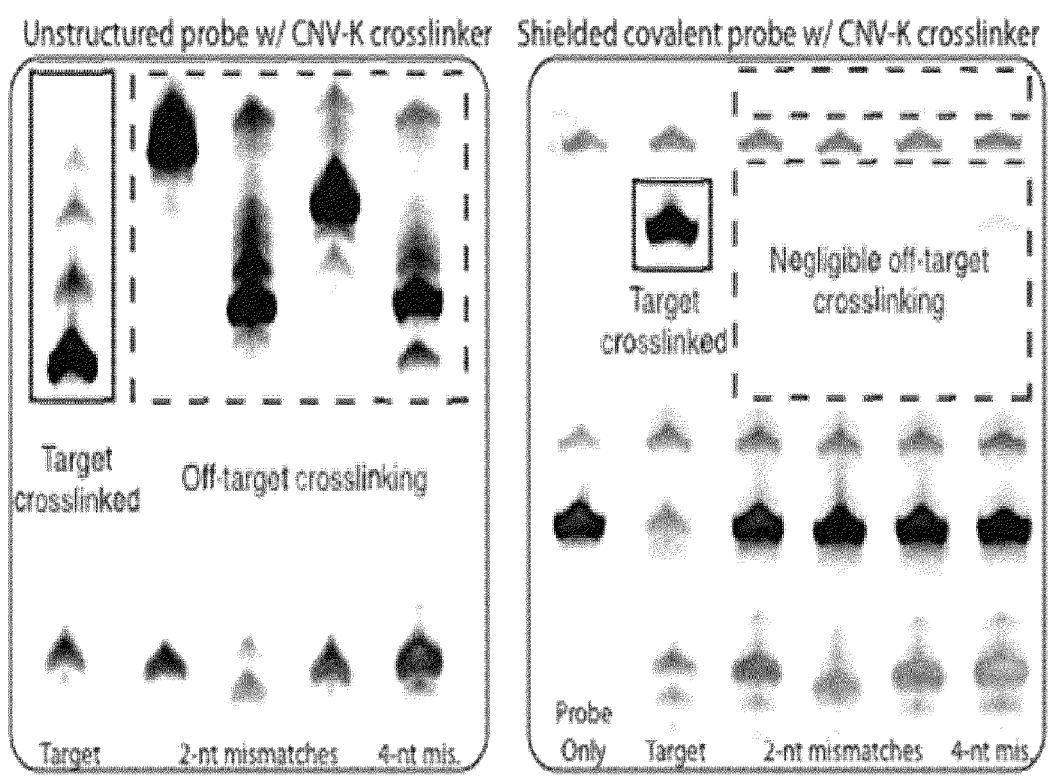
FIG. 10 shows the efficient and selective crosslinking of shielded covalent probes using the CNV-K crosslinker.

As can be seen in FIG. 10, the correct target was crosslinked with greater than 94% yield by both traditional unstructured and shielded covalent probes. However, the shielded covalent probes effectively discriminated against 2 and 4 nucleotide mismatch decoy targets, while the traditional probe crosslinks to both the correct target and the mismatched targets.

Example 8

Antibiotic Therapy

A patient is identified that is suffering from a bacterial infection. A cross-linking probe is prepared that comprises an initiator region and a probe region that are complementary to a portion of a bacterial gene or regulatory nucleic acid from the infectious species that is necessary for the bacterial life cycle or replication (for example, a bacterial house-keeping gene, or a bacterial ribosomal RNA). The probe additionally comprises a blocking region that forms a duplex with the probe region and shields one or more cross-linkers that are associated with the probe region. The cross-linkers are intrinsically active such that they are able to cross-link the target once the blocking region is displaced and the probe region hybridizes to the target.

The cross-linking probes are introduced in vivo into the patient where they are taken up in the bacterial cells and contact the target nucleic acid. Recognition between the initiator region and target allows for branch migration up the cross-linking probe and separation of the probe region from the blocking region. This then allows for the base-pairing of the probe region (and initiator region) to the target nucleic acid. The cross-linker molecules within the probe region are thus activated and cross-link the probe region to the target nucleic acid. The cross linking blocks expression of the targeted gene and causes death of the bacteria or inhibits replication.

Unlike a traditional small-molecule antibiotic, if the bacteria evolves resistance to the shielded covalent probe antibiotic (e.g., by mutating the target nucleic acid so that it is no longer recognized by the shielded covalent probe), the sequence of the shielded covalent probe can be updated to create a new drug that kills the resistant bacteria.

Furthermore, by introducing a therapeutic cocktail comprised of multiple shielded covalent probes, each targeting different nucleic acid targets within the bacteria (such that silencing of any of these targets is sufficient to kill the bacteria), it becomes very difficult for the bacteria to evolve away from the therapy because this would require simultaneous mutation of multiple nucleic acid targets within the bacteria.

While the present teachings have been described in terms of these exemplary embodiments, the skilled artisan will readily understand that numerous variations and modifications of these exemplary embodiments are possible without undue experimentation. All such variations and modifications are within the scope of the current teachings.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein.

Unless otherwise indicated, the singular use of various words, including the term "an" or "an" denotes both the option of a single or more than one. In addition, the use of the term "and/or" denotes various embodiments that include: both options, either option in the alternative, or the combination of either option in the alternative and both options. When describing various combinations, kits, probes, methods, etc., it will be understood that unless otherwise stated, the combinations are described as comprising, consisting of, and consisting essentially of. This does not apply to the claims or to situations in the specification where the term "consisting of" is used.

Incorporation by Reference

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

Equivalents

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A cross-linking probe comprising:
   a nucleic acid initiator region that is able to bind to a first portion of a target nucleic acid;
   a nucleic acid probe region, wherein the probe region is linked to the initiator region and is able to bind to a second portion of the target nucleic acid that is contiguous with the first portion;
   one or more cross-linkers that are part of the probe region, wherein the cross-linker is capable of forming a covalent bond to the target nucleic acid when the nucleic acid initiator region is bound to the first portion of the target nucleic acid and the probe region is bound to the second portion of the target nucleic acid; and
   a blocking region that is hybridized to the probe region.

2. The cross-linking probe of claim 1, wherein the initiator region is complementary to the first portion of the target nucleic acid.

3. The cross-linking probe of claim 1, wherein the probe region is complementary to the second portion of the target nucleic acid.

4. The cross-linking probe of claim 1, further comprising a loop region that links the probe region to the blocking region.

5. The cross-linking probe of claim 1, wherein at least one cross-linker is an activatable cross-linker.

6. The cross-linking probe of claim 5, wherein the activatable cross-linker is light activatable.

7. The cross-linking probe of claim 5, wherein the activatable cross-linker is conformationally activatable.

8. The cross-linking probe of claim 1, wherein at least one of the cross-linkers is selected from the group consisting of 4-Thio-dT and CNV-K.

9. The cross-linking probe of claim 1, wherein the probe region comprises two or more cross linkers.

10. The cross-linking probe of claim 1, wherein the probe region comprises at least one nucleotide on each side of the cross-linker.

11. The cross-linking probe of claim 1, wherein the probe region is immediately adjacent to the initiator region.

12. The cross-linking probe of claim 1, wherein the initiator region is a sticky end.

* * * * *

UNITED STATES PATENT AND TRADEMARK OFFICE
CERTIFICATE OF CORRECTION

| | | |
|---|---|---|
| PATENT NO. | : 8,658,780 B2 | Page 1 of 1 |
| APPLICATION NO. | : 13/016811 | |
| DATED | : February 25, 2014 | |
| INVENTOR(S) | : Niles A. Pierce et al. | |

It is certified that error appears in the above-identified patent and that said Letters Patent is hereby corrected as shown below:

In the specification

Column 1, Line 15, under STATEMENT REGARDING FEDERALLY SPONSORED R&D, please remove "This invention was made with government support under grant nos. NIH 5R01EB006192-04 and NIH P50 HG004071 awarded by the National Institutes of Health. The government has certain rights in this invention."

and insert therefore,

-- This invention was made with government support under Grant Nos. NIH 5R01EB006192-04, NIH P50 HG004071, and CA140759 awarded by the National Institutes of Health. The government has certain rights in the invention. --.

Signed and Sealed this
Seventeenth Day of November, 2015

Michelle K. Lee
*Director of the United States Patent and Trademark Office*

SEQUENCE LISTING

```
<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
actaaccgat agcggctacc g                                        21

<210> SEQ ID NO 2
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 1
<223> OTHER INFORMATION: Modified with either 5' terminal
      trimethylpsoralen PA or SPB, amino-dT conjugate

<400> SEQUENCE: 2
tagccgctat cggttagt                                            18

<210> SEQ ID NO 3
<211> LENGTH: 23
<212> TYPE: DNA
<213> ORGANISM: Artificial Sequence
<220> FEATURE:
<223> OTHER INFORMATION: target oligonucleotide

<400> SEQUENCE: 3
catgtcaacc gttcctgcga gta                                      23

<210> SEQ ID NO 4
<211> LENGTH: 23
<212> TYPE: DNA
<213> ORGANISM: Artificial Sequence
<220> FEATURE:
<223> OTHER INFORMATION: decoy target oligonucleotide
```

```
<400> SEQUENCE: 4
catgtcaacc gttcctggaa gta                                               23

<210> SEQ ID NO 5
<211> LENGTH: 23
<212> TYPE: DNA
<213> ORGANISM: Artificial Sequence
<220> FEATURE:
<223> OTHER INFORMATION: decoy target oligonucleotide

<400> SEQUENCE: 5
catgtcaacc gagcctgcga gta                                               23

<210> SEQ ID NO 6
<211> LENGTH: 23
<212> TYPE: DNA
<213> ORGANISM: Artificial Sequence
<220> FEATURE:
<223> OTHER INFORMATION: decoy target oligonucleotide

<400> SEQUENCE: 6
catgtatacc gttcctgcga gta                                               23

<210> SEQ ID NO 7
<211> LENGTH: 23
<212> TYPE: DNA
<213> ORGANISM: Artificial Sequence
<220> FEATURE:
<223> OTHER INFORMATION: decoy target oligonucleotide

<400> SEQUENCE: 7
catgtcaacc gaggatgcga gta                                               23
```